(12) United States Patent
Plishka et al.

(10) Patent No.: US 7,981,090 B2
(45) Date of Patent: Jul. 19, 2011

(54) LUER ACTIVATED DEVICE

(75) Inventors: Michael Plishka, Lake Villa, IL (US); Anthony D. Friend, Algonquin, IL (US); Vincent C. Desecki, Spring Grove, IL (US); Steven C. Jepson, Palatine, IL (US)

(73) Assignees: Baxter International Inc., Deerfield, IL (US); Baxter Healthcare S.A., Gtattpark (Opfikon) (CH)

( * ) Notice: Subject to any disclaimer, the term of this patent is extended or adjusted under 35 U.S.C. 154(b) by 910 days.

(21) Appl. No.: 11/550,578

(22) Filed: Oct. 18, 2006

(65) Prior Publication Data

US 2008/0172003 A1 Jul. 17, 2008

(51) Int. Cl.
*A61M 5/00* (2006.01)
(52) U.S. Cl. ......... 604/249; 604/246; 604/248; 604/905
(58) Field of Classification Search .......... 604/246–256, 604/167; 606/195
See application file for complete search history.

(56) References Cited

U.S. PATENT DOCUMENTS

| | | | |
|---|---|---|---|
| 4,176,588 A | 12/1979 | Baron | |
| 4,334,551 A | 6/1982 | Pfister | |
| 4,413,462 A | 11/1983 | Rose | |
| 4,475,548 A | 10/1984 | Muto | |
| 4,691,929 A | 9/1987 | Neumaier et al. | |
| 4,745,907 A * | 5/1988 | Russel et al. | 600/4 |
| 4,928,212 A | 5/1990 | Benavides | |
| 4,943,896 A | 7/1990 | Johnson | |
| 4,946,445 A | 8/1990 | Lynn | |
| 4,964,855 A | 10/1990 | Todd et al. | |
| 4,973,443 A | 11/1990 | Larson et al. | |
| 4,998,713 A | 3/1991 | Vaillancourt | |
| 4,998,927 A | 3/1991 | Vaillancourt | |
| 5,009,490 A | 4/1991 | Kouno et al. | |
| 5,019,325 A | 5/1991 | Larson et al. | |
| 5,046,456 A | 9/1991 | Heyman et al. | |
| D321,250 S | 10/1991 | Jepson et al. | |
| D321,251 S | 10/1991 | Jepson et al. | |
| 5,064,416 A | 11/1991 | Newgard et al. | |
| 5,065,783 A | 11/1991 | Ogle, II | |
| 5,100,394 A | 3/1992 | Dudar et al. | |
| 5,114,408 A | 5/1992 | Fleischhaker et al. | |
| 5,122,123 A | 6/1992 | Vaillancourt | |
| 5,135,489 A | 8/1992 | Jepson et al. | |
| 5,154,703 A | 10/1992 | Bonaldo | |
| 5,158,554 A | 10/1992 | Jepson et al. | |
| 5,171,234 A | 12/1992 | Jepson et al. | |
| 5,188,620 A | 2/1993 | Jepson et al. | |
| 5,199,947 A | 4/1993 | Lopez et al. | |
| 5,201,717 A | 4/1993 | Wyatt et al. | |
| 5,203,775 A | 4/1993 | Frank et al. | |
| 5,211,638 A | 5/1993 | Dudar et al. | |

(Continued)

FOREIGN PATENT DOCUMENTS

CA 1105959 7/1981

(Continued)

*Primary Examiner* — Theodore J Stigell
*Assistant Examiner* — Imani Hayman
(74) *Attorney, Agent, or Firm* — K&L Gates LLP

(57) ABSTRACT

A luer activated device for infusing and aspirating fluids to and from a variety of fluid systems. The luer activated device includes a housing and employs a variety of valves that permit and prevent the transfer of fluids through the housing into or out of various fluid systems.

14 Claims, 11 Drawing Sheets

U.S. PATENT DOCUMENTS

| | | | |
|---|---|---|---|
| 5,242,393 A | 9/1993 | Brimhall et al. |
| 5,242,425 A | 9/1993 | White et al. |
| 5,242,432 A | 9/1993 | DeFrank |
| 5,251,873 A | 10/1993 | Atkinson et al. |
| 5,256,155 A | 10/1993 | Yerlikaya et al. |
| 5,269,763 A | 12/1993 | Boehmer et al. |
| 5,269,771 A | 12/1993 | Thomas et al. |
| 5,280,876 A | 1/1994 | Atkins |
| 5,290,254 A | 3/1994 | Vaillancourt |
| 5,295,657 A | 3/1994 | Atkinson |
| 5,295,658 A | 3/1994 | Atkinson et al. |
| 5,312,377 A | 5/1994 | Dalton |
| 5,323,264 A | 6/1994 | Kato |
| 5,324,270 A | 6/1994 | Kayan et al. |
| 5,344,414 A | 9/1994 | Lopez et al. |
| 5,360,413 A | 11/1994 | Leason et al. |
| 5,401,245 A | 3/1995 | Haining |
| 5,402,982 A | 4/1995 | Atkinson et al. |
| 5,411,499 A | 5/1995 | Dudar et al. |
| 5,417,673 A | 5/1995 | Gordon |
| 5,470,319 A | 11/1995 | Mayer |
| 5,487,731 A | 1/1996 | Denton |
| 5,514,109 A | 5/1996 | Mollenauer et al. |
| 5,533,708 A | 7/1996 | Atkinson et al. |
| 5,540,661 A | 7/1996 | Tomisaka et al. |
| 5,549,566 A | 8/1996 | Elias et al. |
| 5,549,651 A | 8/1996 | Lynn |
| 5,556,388 A | 9/1996 | Johlin, Jr. |
| 5,578,059 A | 11/1996 | Patzer |
| 5,602,016 A | 2/1997 | Isogai et al. |
| 5,609,584 A | 3/1997 | Gettig et al. |
| 5,616,129 A | 4/1997 | Mayer |
| 5,616,130 A | 4/1997 | Mayer |
| 5,676,346 A | 10/1997 | Leinsing |
| 5,677,141 A | 10/1997 | Isogai et al. |
| 5,685,866 A | 11/1997 | Lopez |
| 5,690,612 A | 11/1997 | Lopez et al. |
| 5,695,466 A | 12/1997 | Lopez et al. |
| 5,699,821 A | 12/1997 | Paradis |
| 5,700,248 A | 12/1997 | Lopez |
| 5,730,418 A | 3/1998 | Feith et al. |
| 5,738,663 A | 4/1998 | Lopez |
| 5,773,272 A | 6/1998 | Isogai et al. |
| RE35,841 E | 7/1998 | Frank et al. |
| 5,788,675 A | 8/1998 | Mayer |
| 5,797,897 A | 8/1998 | Jepson et al. |
| 5,820,601 A | 10/1998 | Mayer |
| 5,836,923 A | 11/1998 | Mayer |
| 5,865,807 A | 2/1999 | Blake, III |
| 5,873,862 A | 2/1999 | Lopez |
| 5,901,942 A | 5/1999 | Lopez |
| 5,928,204 A | 7/1999 | Lopez |
| 5,957,898 A | 9/1999 | Jepson et al. |
| 5,967,490 A | 10/1999 | Pike |
| 5,971,965 A | 10/1999 | Mayer |
| RE36,587 E | 2/2000 | Tanaka et al. |
| 6,019,748 A | 2/2000 | Lopez |
| 6,029,946 A | 2/2000 | Doyle |
| 6,036,171 A | 3/2000 | Weinheimer et al. |
| 6,039,302 A | 3/2000 | Cote, Sr. et al. |
| RE36,661 E | 4/2000 | Tanaka et al. |
| 6,048,335 A | 4/2000 | Mayer |
| 6,089,541 A | 7/2000 | Weinheimer et al. |
| 6,113,068 A | 9/2000 | Ryan |
| 6,132,403 A | 10/2000 | Lopez |
| 6,132,404 A | 10/2000 | Lopez |
| 6,146,396 A | 11/2000 | Konya et al. |
| 6,152,900 A | 11/2000 | Mayer |
| 6,162,251 A | 12/2000 | Kredovski |
| 6,171,287 B1 | 1/2001 | Lynn et al. |
| 6,177,037 B1 | 1/2001 | Mayer |
| 6,183,448 B1 | 2/2001 | Mayer |
| 6,187,476 B1 | 2/2001 | Pyun et al. |
| 6,210,624 B1 | 4/2001 | Mayer |
| 6,228,069 B1 | 5/2001 | Barth et al. |
| 6,245,048 B1 | 6/2001 | Fangrow, Jr. et al. |
| 6,261,268 B1 | 7/2001 | Mayer |
| 6,261,282 B1 | 7/2001 | Jepson et al. |
| 6,290,206 B1 | 9/2001 | Doyle |
| 6,299,132 B1 | 10/2001 | Weinheimer et al. |
| 6,325,782 B1 | 12/2001 | Lopez |
| 6,341,802 B1 | 1/2002 | Matkovich |
| 6,344,033 B1 | 2/2002 | Jepson et al. |
| 6,355,023 B1 | 3/2002 | Roth et al. |
| 6,364,869 B1 | 4/2002 | Bonaldo |
| 6,374,876 B2 | 4/2002 | Bynum |
| 6,383,168 B1 | 5/2002 | Landau et al. |
| 6,390,120 B1 | 5/2002 | Guala |
| 6,390,130 B1 | 5/2002 | Guala |
| 6,394,983 B1 | 5/2002 | Mayoral et al. |
| 6,394,992 B1 | 5/2002 | Sjoholm |
| 6,402,723 B1 | 6/2002 | Lampropoulos et al. |
| 6,408,897 B1 | 6/2002 | Laurent et al. |
| 6,409,707 B1 | 6/2002 | Guala |
| 6,409,708 B1 | 6/2002 | Wessman |
| 6,423,053 B1 | 7/2002 | Lee |
| 6,428,520 B1 | 8/2002 | Lopez et al. |
| 6,440,107 B1 | 8/2002 | Trombley, III et al. |
| 6,467,732 B2 | 10/2002 | Tsukahara et al. |
| 6,481,756 B1 | 11/2002 | Field et al. |
| 6,482,188 B1 | 11/2002 | Rogers et al. |
| 6,485,472 B1 | 11/2002 | Richmond |
| 6,486,630 B2 | 11/2002 | Takagi |
| 6,491,668 B1 | 12/2002 | Paradis |
| 6,508,807 B1 | 1/2003 | Peters |
| 6,520,932 B2 | 2/2003 | Taylor |
| 6,536,805 B2 | 3/2003 | Matkovich |
| 6,537,258 B1 | 3/2003 | Guala |
| 6,539,248 B1 | 3/2003 | Moroski |
| 6,541,802 B2 | 4/2003 | Doyle |
| 6,543,745 B1 | 4/2003 | Enerson |
| 6,544,236 B1 | 4/2003 | Cragg et al. |
| 6,569,118 B2 | 5/2003 | Johnson et al. |
| 6,569,125 B2 | 5/2003 | Jepson et al. |
| RE38,145 E | 6/2003 | Lynn |
| 6,572,590 B1 | 6/2003 | Stevens et al. |
| 6,572,591 B2 | 6/2003 | Mayer |
| 6,572,592 B1 | 6/2003 | Lopez |
| 6,581,906 B2 | 6/2003 | Pott et al. |
| 6,585,229 B2 | 7/2003 | Cote, Sr. et al. |
| 6,595,954 B1 | 7/2003 | Luther et al. |
| 6,595,964 B2 | 7/2003 | Finley et al. |
| 6,599,273 B1 | 7/2003 | Lopez |
| 6,605,076 B1 | 8/2003 | Jepson et al. |
| 6,609,696 B2 | 8/2003 | Enerson |
| 6,620,119 B1 | 9/2003 | Utterberg et al. |
| 6,626,418 B2 | 9/2003 | Kiehne |
| 6,634,033 B2 | 10/2003 | Mizuno et al. |
| 6,635,044 B2 | 10/2003 | Lopez |
| 6,638,244 B1 | 10/2003 | Reynolds |
| 6,638,258 B2 | 10/2003 | Schwartz et al. |
| 6,651,956 B2 | 11/2003 | Miller |
| 6,655,655 B1 | 12/2003 | Matkovich et al. |
| 6,666,839 B2 | 12/2003 | Utterberg et al. |
| 6,669,673 B2 | 12/2003 | Lopez |
| 6,669,681 B2 | 12/2003 | Jepson et al. |
| 6,673,059 B2 | 1/2004 | Guala |
| 6,679,529 B2 | 1/2004 | Johnson et al. |
| 6,681,810 B2 | 1/2004 | Weston |
| 6,682,509 B2 | 1/2004 | Lopez |
| 6,695,817 B1 | 2/2004 | Fangrow, Jr. |
| 6,699,222 B1 | 3/2004 | Jones et al. |
| 6,706,022 B1 | 3/2004 | Leinsing et al. |
| 6,716,187 B1 | 4/2004 | Jorgensen et al. |
| 6,716,189 B1 | 4/2004 | Jarvik et al. |
| 6,722,705 B2 | 4/2004 | Korkor |
| 6,723,074 B1 | 4/2004 | Halseth |
| 6,726,651 B1 | 4/2004 | Robinson et al. |
| 6,726,672 B1 | 4/2004 | Hanly et al. |
| 6,730,883 B2 | 5/2004 | Brown et al. |
| 6,745,998 B2 | 6/2004 | Doyle |
| 6,746,438 B1 | 6/2004 | Arnissolle |
| 6,755,391 B2 | 6/2004 | Newton et al. |
| 6,758,833 B2 | 7/2004 | Lopez |
| 6,770,051 B2 | 8/2004 | Hughes et al. |
| 6,802,490 B2 | 10/2004 | Leinsing et al. |
| 6,802,836 B2 | 10/2004 | Bouphavichith et al. |

| | | | | | |
|---|---|---|---|---|---|
| 6,808,161 B1 | 10/2004 | Hishikawa | 2002/0138047 A1 | 9/2002 | Lopez |
| 6,808,509 B1 | 10/2004 | Davey | 2002/0143300 A1 | 10/2002 | Trombley et al. |
| 6,811,139 B2 | 11/2004 | Hishikawa | 2002/0143301 A1 | 10/2002 | Lopez |
| 6,814,726 B1 | 11/2004 | Lauer | 2002/0147429 A1 | 10/2002 | Cowan et al. |
| 6,827,709 B2 | 12/2004 | Fujii | 2002/0147431 A1 | 10/2002 | Lopez et al. |
| 6,827,710 B1 | 12/2004 | Mooney et al. | 2002/0153503 A1 | 10/2002 | Newton et al. |
| 6,834,842 B2 | 12/2004 | Houde | 2002/0156431 A1 | 10/2002 | Feith et al. |
| 6,840,501 B2 | 1/2005 | Doyle | 2002/0161334 A1 | 10/2002 | Castellano et al. |
| 6,843,513 B2 | 1/2005 | Guala | 2002/0193752 A1 | 12/2002 | Lynn |
| 6,866,656 B2 | 3/2005 | Tingey et al. | 2003/0028156 A1 | 2/2003 | Juliar |
| 6,869,426 B2 | 3/2005 | Ganem | 2003/0032940 A1 | 2/2003 | Doyle |
| 6,871,087 B1 | 3/2005 | Hughes et al. | 2003/0036735 A1 | 2/2003 | Jepson et al. |
| 6,874,522 B2 | 4/2005 | Anderson et al. | 2003/0050610 A1 | 3/2003 | Newton et al. |
| 6,878,905 B2 | 4/2005 | Brown et al. | 2003/0060779 A1 | 3/2003 | Richmond |
| 6,880,801 B2 | 4/2005 | Matkovich et al. | 2003/0060804 A1 | 3/2003 | Vaillancourt |
| 6,883,778 B1 | 4/2005 | Newton et al. | 2003/0066978 A1 | 4/2003 | Enerson |
| 6,893,056 B2 | 5/2005 | Guala | 2003/0066980 A1 | 4/2003 | Hishikawa |
| 6,902,207 B2 | 6/2005 | Lickliter | 2003/0085372 A1 | 5/2003 | Newton |
| 6,908,459 B2 | 6/2005 | Harding et al. | 2003/0093061 A1 | 5/2003 | Ganem |
| 6,911,025 B2 | 6/2005 | Miyahara | 2003/0098430 A1 | 5/2003 | Leinsing et al. |
| 6,916,309 B2 | 7/2005 | Fangrow, Jr. | 2003/0105452 A1 | 6/2003 | Mayer |
| 6,918,500 B2 | 7/2005 | Okiyama | 2003/0109853 A1 | 6/2003 | Harding et al. |
| 6,932,795 B2 | 8/2005 | Lopez et al. | 2003/0120221 A1 | 6/2003 | Vaillancourt |
| 6,953,450 B2 | 10/2005 | Baldwin et al. | 2003/0127620 A1 | 7/2003 | Houde |
| 6,955,669 B2 | 10/2005 | Curutcharry | 2003/0141477 A1 | 7/2003 | Miller |
| 6,960,198 B2 | 11/2005 | Sarmiento | 2003/0144626 A1 | 7/2003 | Hanson et al. |
| 6,964,406 B2 | 11/2005 | Doyle | 2003/0144647 A1 | 7/2003 | Miyahara |
| 6,969,381 B2 | 11/2005 | Voorhees | 2003/0181850 A1 | 9/2003 | Diamond et al. |
| 6,972,001 B2 | 12/2005 | Emig et al. | 2003/0181854 A1 | 9/2003 | Sauvageau |
| 6,974,446 B2 | 12/2005 | Hommann et al. | 2003/0183795 A1 | 10/2003 | Doyle |
| 6,994,315 B2 | 2/2006 | Ryan et al. | 2003/0195478 A1 | 10/2003 | Russo |
| 7,004,934 B2 | 2/2006 | Vaillancourt | 2003/0199835 A1 | 10/2003 | Leinsing et al. |
| 7,008,406 B2 | 3/2006 | Mayer | 2003/0208165 A1 | 11/2003 | Christensen et al. |
| 7,014,169 B2 | 3/2006 | Newton et al. | 2003/0209681 A1 | 11/2003 | Leinsing et al. |
| 7,025,744 B2 | 4/2006 | Utterberg et al. | 2003/0216712 A1 | 11/2003 | Kessler et al. |
| 7,033,339 B1 | 4/2006 | Lynn | 2003/0225379 A1 | 12/2003 | Schaffer et al. |
| 7,037,302 B2 | 5/2006 | Vaillancourt et al. | 2003/0236497 A1 | 12/2003 | Fremming et al. |
| 7,041,087 B2 | 5/2006 | Henderson et al. | 2004/0006330 A1 | 1/2004 | Fangrow |
| 7,044,441 B2 | 5/2006 | Doyle | 2004/0019344 A1 | 1/2004 | Peterson et al. |
| 7,044,937 B1 | 5/2006 | Kirwan et al. | 2004/0030321 A1 | 2/2004 | Fangrow |
| 7,081,600 B2 | 7/2006 | Brown et al. | 2004/0068238 A1 | 4/2004 | Utterberg et al. |
| 7,083,605 B2 | 8/2006 | Miyahara | 2004/0068239 A1 | 4/2004 | Utterberg |
| 7,090,191 B2 | 8/2006 | Matkovich et al. | 2004/0073174 A1 | 4/2004 | Lopez |
| 7,097,209 B2 | 8/2006 | Sparrman et al. | 2004/0073176 A1 | 4/2004 | Utterberg |
| 7,100,891 B2 | 9/2006 | Doyle | 2004/0092886 A1 | 5/2004 | Mayer |
| 7,104,520 B2 | 9/2006 | Leinsing et al. | 2004/0102738 A1 | 5/2004 | Dikeman et al. |
| RE39,334 E | 10/2006 | Lynn | 2004/0111078 A1 | 6/2004 | Miyahara |
| 7,114,701 B2 | 10/2006 | Peppel | 2004/0116869 A1 | 6/2004 | Heinz et al. |
| 7,118,560 B2 | 10/2006 | Bonaldo | 2004/0122418 A1 | 6/2004 | Voorhees |
| 7,128,348 B2 | 10/2006 | Kawamura et al. | 2004/0124388 A1 | 7/2004 | Kiehne |
| 7,137,974 B2 | 11/2006 | Almasian et al. | 2004/0124389 A1 | 7/2004 | Phillips |
| 7,140,592 B2 | 11/2006 | Phillips | 2004/0138641 A1 | 7/2004 | Patzer |
| 7,153,296 B2 | 12/2006 | Mitchell | 2004/0162517 A1 | 8/2004 | Furst et al. |
| 7,156,826 B2 | 1/2007 | Ishii et al. | 2004/0162540 A1 | 8/2004 | Walenciak et al. |
| 7,160,272 B1 | 1/2007 | Eyal et al. | 2004/0171993 A1 | 9/2004 | Bonaldo |
| RE39,499 E | 2/2007 | Racz | 2004/0172006 A1 | 9/2004 | Bonaldo |
| 7,172,572 B2 | 2/2007 | Diamond et al. | 2004/0186458 A1 | 9/2004 | Hiejima et al. |
| 7,174,923 B2 | 2/2007 | Schorn et al. | 2004/0193119 A1 | 9/2004 | Canaud et al. |
| 7,175,615 B2 | 2/2007 | Hanly et al. | 2004/0199126 A1 | 10/2004 | Harding et al. |
| 7,182,313 B2 | 2/2007 | Doyle | 2004/0204699 A1 | 10/2004 | Hanly et al. |
| 7,184,825 B2 | 2/2007 | Leinsing et al. | 2004/0206924 A1 | 10/2004 | Newton et al. |
| 2001/0045539 A1 | 11/2001 | Doyle | 2004/0210194 A1 | 10/2004 | Bonnette et al. |
| 2001/0049508 A1 | 12/2001 | Fangrow et al. | 2004/0225274 A1 | 11/2004 | Jansen et al. |
| 2001/0051791 A1 | 12/2001 | Azzolini | 2004/0227120 A1 | 11/2004 | Raybuck |
| 2001/0051793 A1 | 12/2001 | Weston | 2004/0236314 A1 | 11/2004 | Saab |
| 2002/0007157 A1 | 1/2002 | Azzolini | 2004/0243065 A1 | 12/2004 | McConnell et al. |
| 2002/0024036 A1 | 2/2002 | Rohrbough et al. | 2004/0243069 A1 | 12/2004 | Feith et al. |
| 2002/0032433 A1 | 3/2002 | Lopez | 2004/0243070 A1 | 12/2004 | Lopez |
| 2002/0038114 A1 | 3/2002 | Segura | 2004/0249349 A1 | 12/2004 | Wentling |
| 2002/0062106 A1 | 5/2002 | Chu et al. | 2004/0254534 A1 | 12/2004 | Bjorkman et al. |
| 2002/0082586 A1 | 6/2002 | Finley et al. | 2004/0260243 A1 | 12/2004 | Rickerd |
| 2002/0099360 A1 | 7/2002 | Bierman | 2004/0260266 A1 | 12/2004 | Cuschieri et al. |
| 2002/0108614 A1 | 8/2002 | Schultz | 2005/0010168 A1 | 1/2005 | Kendall |
| 2002/0115981 A1 | 8/2002 | Wessman | 2005/0015070 A1 | 1/2005 | Delnevo et al. |
| 2002/0115984 A1 | 8/2002 | Guala | 2005/0021000 A1 | 1/2005 | Adair et al. |
| 2002/0117645 A1 | 8/2002 | Kiehne | 2005/0033267 A1 | 2/2005 | Decaria |
| 2002/0128595 A1 | 9/2002 | Weston et al. | 2005/0033268 A1 | 2/2005 | Decaria |
| 2002/0128607 A1 | 9/2002 | Haury et al. | 2005/0033269 A1 | 2/2005 | Decaria |
| 2002/0133124 A1 | 9/2002 | Leinsing et al. | 2005/0038397 A1 | 2/2005 | Newton et al. |

| | | | | | | |
|---|---|---|---|---|---|---|
| 2005/0059952 A1 | 3/2005 | Giuliano et al. | | 2006/0264908 A1 | 11/2006 | Ishii et al. |
| 2005/0087715 A1 | 4/2005 | Doyle | | 2006/0264909 A1 | 11/2006 | Fangrow |
| 2005/0090805 A1 | 4/2005 | Shaw et al. | | 2006/0264910 A1 | 11/2006 | Fangrow |
| 2005/0096585 A1 | 5/2005 | Schon et al. | | 2006/0270999 A1 | 11/2006 | Fangrow |
| 2005/0107770 A1 | 5/2005 | Schweikert et al. | | 2006/0271012 A1 | 11/2006 | Canoud et al. |
| 2005/0119613 A1 | 6/2005 | Moenning et al. | | 2006/0271015 A1 | 11/2006 | Mantell |
| 2005/0121638 A1 | 6/2005 | Doyle | | 2006/0271016 A1 | 11/2006 | Fangrow |
| 2005/0124935 A1 | 6/2005 | McMicheal | | 2006/0276757 A1 | 12/2006 | Fangrow |
| 2005/0124942 A1 | 6/2005 | Richmond | | 2006/0276758 A1 | 12/2006 | Fangrow |
| 2005/0124943 A1 | 6/2005 | Yang | | 2006/0287638 A1 | 12/2006 | Aneas |
| 2005/0154372 A1 | 7/2005 | Minezaki | | 2006/0287639 A1 | 12/2006 | Sharp |
| 2005/0159710 A1 | 7/2005 | Utterberg | | 2006/0293629 A1 | 12/2006 | Cote et al. |
| 2005/0165365 A1 | 7/2005 | Newton et al. | | 2006/0293640 A1 | 12/2006 | Greco |
| 2005/0171487 A1 | 8/2005 | Haury et al. | | 2007/0032775 A1 | 2/2007 | Niedospial et al. |
| 2005/0209555 A1 | 9/2005 | Middleton et al. | | 2007/0032776 A1 | 2/2007 | Skinner et al. |
| 2005/0228362 A1 | 10/2005 | Vaillancourt | | 2007/0038189 A1 | 2/2007 | Bartholomew |
| 2005/0256460 A1 | 11/2005 | Rome et al. | | 2007/0043334 A1 | 2/2007 | Guala |
| 2005/0256461 A1 | 11/2005 | DiFiore et al. | | 2007/0060898 A1 | 3/2007 | Shaughnessy et al. |
| 2005/0261637 A1 | 11/2005 | Miller | | 2007/0060902 A1 | 3/2007 | Brandenburger et al. |
| 2005/0261665 A1 | 11/2005 | Voorhees | | 2007/0060904 A1 | 3/2007 | Vedrine et al. |
| 2005/0267445 A1 | 12/2005 | Mendels | | 2007/0073242 A1 | 3/2007 | Andersen et al. |
| 2006/0015086 A1 | 1/2006 | Rasmussen et al. | | 2007/0078393 A1 | 4/2007 | Lynch et al. |
| 2006/0025724 A1 | 2/2006 | Chen | | 2007/0078429 A1 | 4/2007 | Sharp |
| 2006/0025751 A1 | 2/2006 | Roy et al. | | 2007/0083157 A1 | 4/2007 | Belley et al. |
| 2006/0027270 A1 | 2/2006 | Truitt et al. | | 2007/0088252 A1 | 4/2007 | Pestotnik et al. |
| 2006/0047251 A1 | 3/2006 | Bickford-Smith et al. | | 2007/0088292 A1 | 4/2007 | Fangrow |
| 2006/0074386 A1 | 4/2006 | Wollmann | | 2007/0088293 A1 | 4/2007 | Fangrow |
| 2006/0089603 A1 | 4/2006 | Truitt et al. | | 2007/0088294 A1 | 4/2007 | Fangrow |
| 2006/0089604 A1 | 4/2006 | Guerrero | | 2007/0088313 A1 | 4/2007 | Zinger et al. |
| 2006/0089605 A1 | 4/2006 | Fitzgerald | | 2007/0088324 A1 | 4/2007 | Fangrow |
| 2006/0111694 A1 | 5/2006 | Fukai et al. | | 2007/0088325 A1 | 4/2007 | Fangrow |
| 2006/0129109 A1 | 6/2006 | Shaw et al. | | 2007/0088327 A1 | 4/2007 | Guala |
| 2006/0129112 A1 | 6/2006 | Lynn | | 2007/0093764 A1 | 4/2007 | Guererro |
| 2006/0142735 A1 | 6/2006 | Whitley | | 2007/0100294 A1 | 5/2007 | Sugita et al. |
| 2006/0149213 A1 | 7/2006 | Raybuck | | 2007/0112311 A1 | 5/2007 | Harding et al. |
| 2006/0161115 A1 | 7/2006 | Fangrow | | 2007/0112312 A1 | 5/2007 | Fangrow |
| 2006/0173420 A1 | 8/2006 | Fangrow | | 2007/0112313 A1 | 5/2007 | Fangrow |
| 2006/0178645 A1 | 8/2006 | Peppel | | 2007/0112314 A1 | 5/2007 | Harding |
| 2006/0184139 A1 | 8/2006 | Quigley et al. | | 2007/0112332 A1 | 5/2007 | Harding et al. |
| 2006/0184140 A1 | 8/2006 | Okiyama | | 2007/0112333 A1 | 5/2007 | Hoang et al. |
| 2006/0200072 A1 | 9/2006 | Peppel | | 2007/0129705 A1 | 6/2007 | Trombley, III et al. |
| 2006/0200095 A1 | 9/2006 | Steube | | 2007/0156112 A1 | 7/2007 | Walsh |
| 2006/0200096 A1 | 9/2006 | Fangrow | | 2007/0156118 A1 | 7/2007 | Ramsey et al. |
| 2006/0206058 A1 | 9/2006 | Lopez | | | | |
| 2006/0206059 A1 | 9/2006 | Lopez | | | | |

FOREIGN PATENT DOCUMENTS

| | | | |
|---|---|---|---|
| 2006/0211997 A1 | 9/2006 | Fangrow | |
| 2006/0211998 A1 | 9/2006 | Fangrow | |
| 2006/0211999 A1 | 9/2006 | Fangrow | DE | 855319 | 11/1952 |
| 2006/0212000 A1 | 9/2006 | Fangrow | DE | 8425197 | 10/1985 |
| 2006/0212001 A1 | 9/2006 | Fangrow | DE | 3740269 | 6/1989 |
| 2006/0212002 A1 | 9/2006 | Fangrow | EP | 0114677 | 8/1984 |
| 2006/0212003 A1 | 9/2006 | Fangrow | EP | 0237321 | 9/1987 |
| 2006/0212005 A1 | 9/2006 | Fangrow | EP | 0309771 | 4/1989 |
| 2006/0212006 A1 | 9/2006 | Fangrow et al. | EP | 0367549 | 10/1989 |
| 2006/0217671 A1 | 9/2006 | Peppel | EP | 0399119 | 11/1990 |
| 2006/0217679 A1 | 9/2006 | Hanly et al. | EP | 0438909 | 12/1990 |
| 2006/0217683 A1 | 9/2006 | Patania | EP | 0446463 | 12/1990 |
| 2006/0229571 A1 | 10/2006 | Peppel | EP | 1733749 A1 | 12/2006 |
| 2006/0229590 A1 | 10/2006 | Roy | GB | 2034185 | 6/1980 |
| 2006/0264842 A1 | 11/2006 | Fangrow | WO | 86/01712 | 3/1986 |
| 2006/0264843 A1 | 11/2006 | Fangrow | WO | 86/03416 | 6/1986 |
| 2006/0264844 A1 | 11/2006 | Fangrow | WO | 93/11828 | 6/1993 |
| 2006/0264845 A1 | 11/2006 | Lopez | WO | 97/21463 | 6/1997 |
| 2006/0264846 A1 | 11/2006 | Lopez | WO | 97/21464 | 6/1997 |
| 2006/0264847 A1 | 11/2006 | Lopez | WO | 98/26835 | 6/1998 |
| 2006/0264848 A1 | 11/2006 | Fangrow | WO | 99/58186 | 11/1999 |
| 2006/0264890 A1 | 11/2006 | Moberg et al. | WO | 02/04065 | 1/2002 |
| 2006/0264891 A1 | 11/2006 | Lopez | WO | 03/086528 | 10/2003 |
| 2006/0264892 A1 | 11/2006 | Lopez | WO | PCT/US2007/080183 | 3/2008 |
| 2006/0264894 A1 | 11/2006 | Moberg et al. | | | |

* cited by examiner

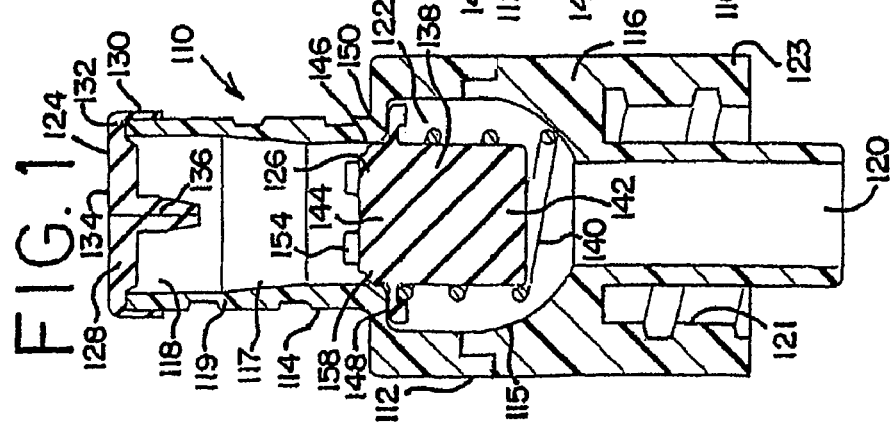

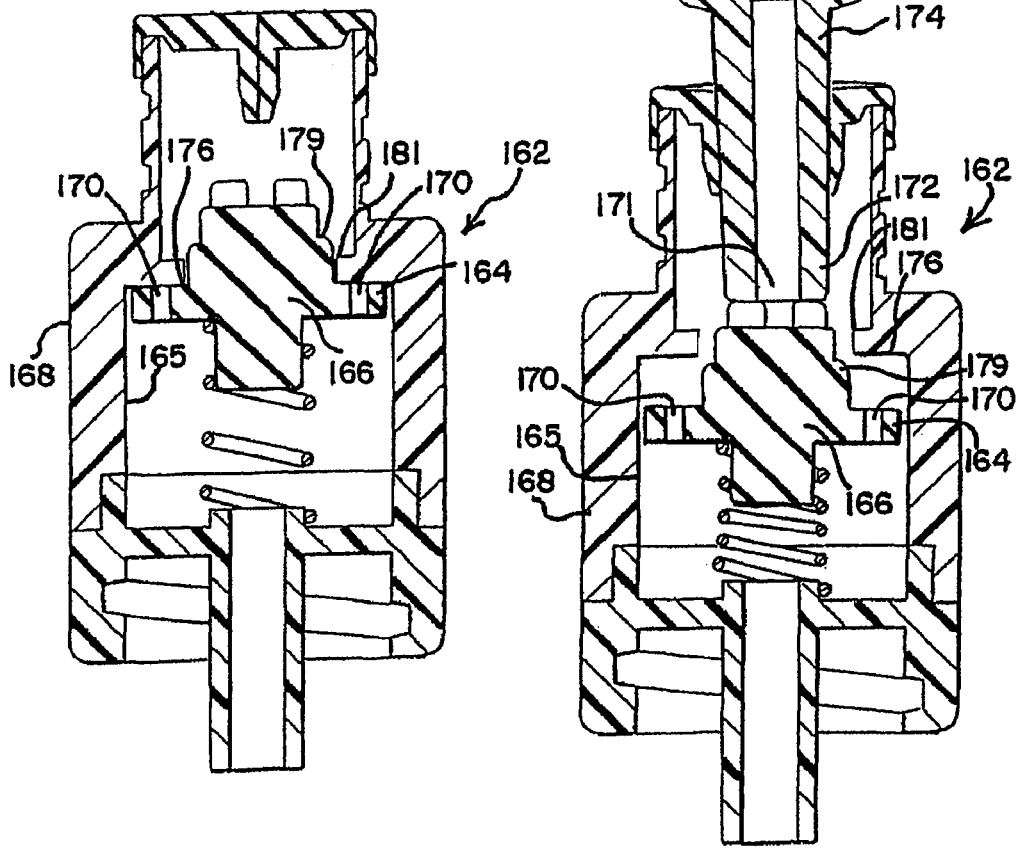
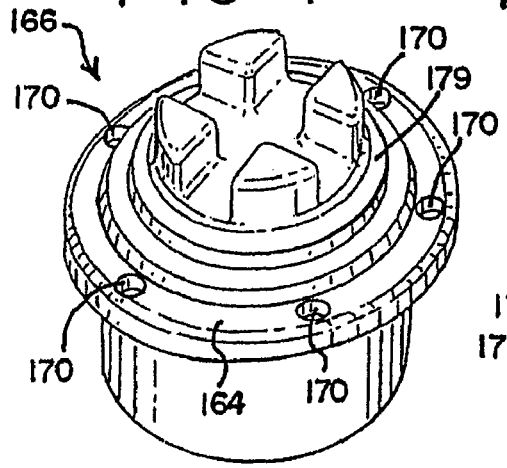
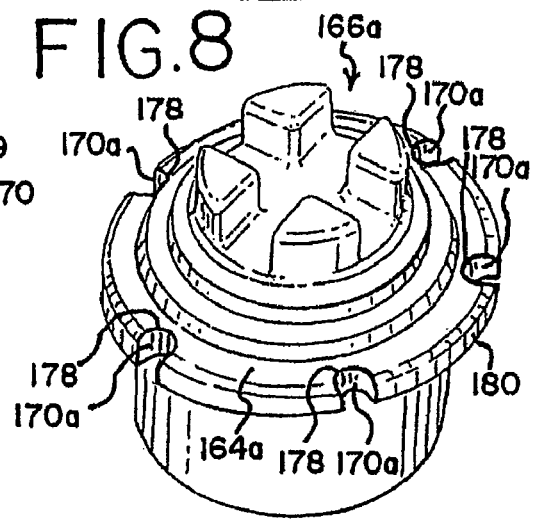

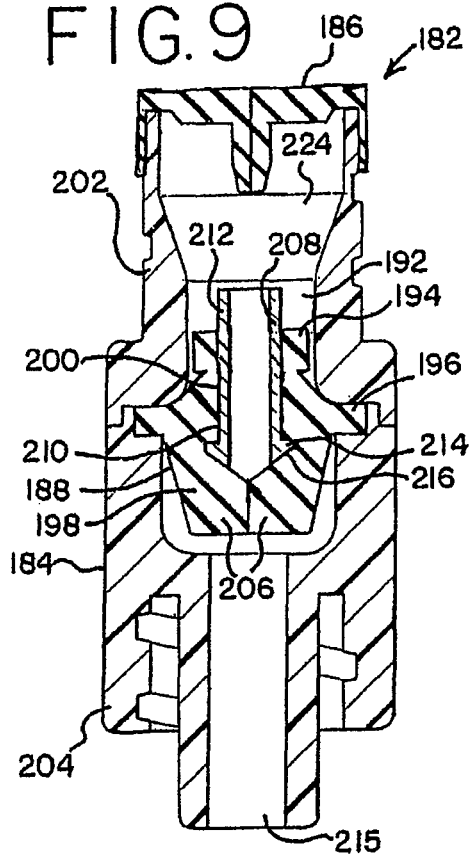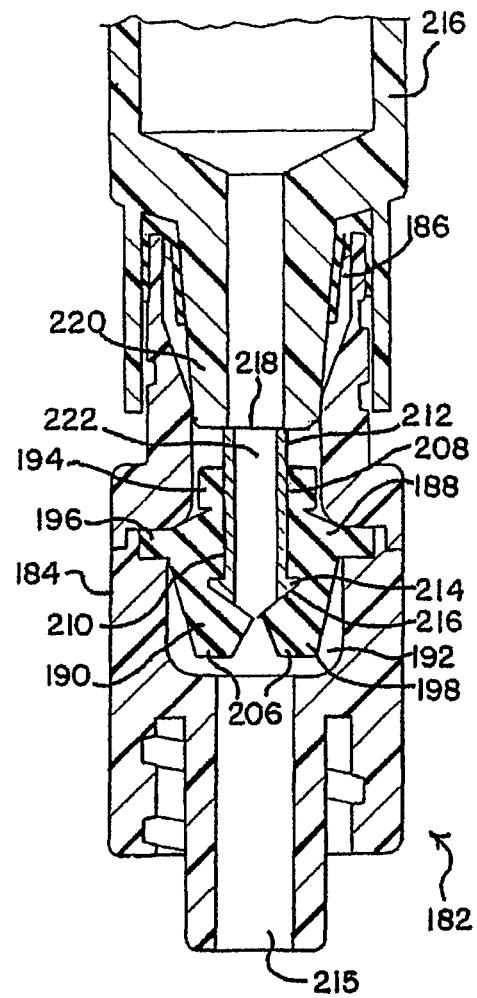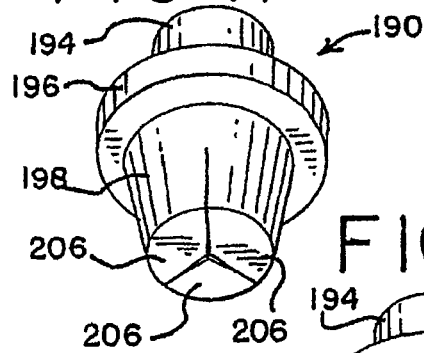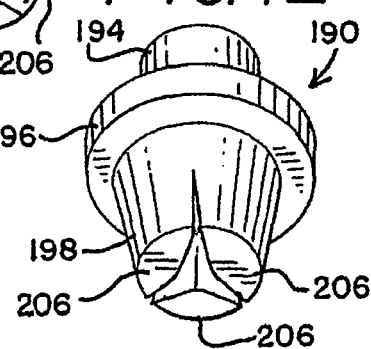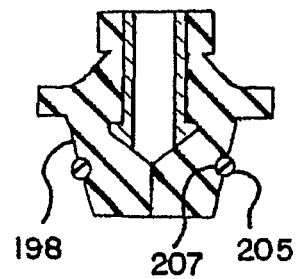

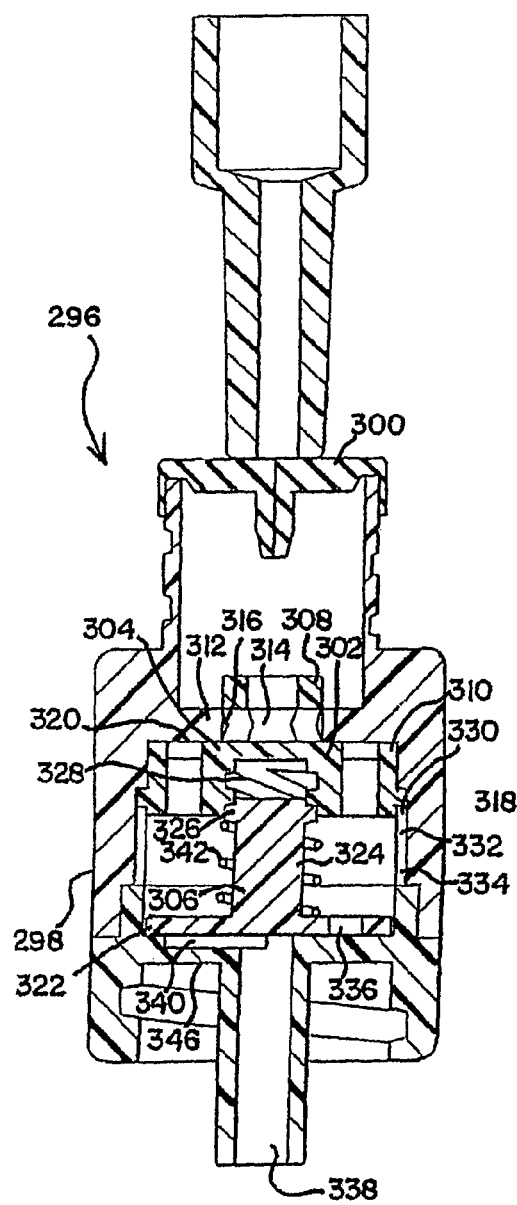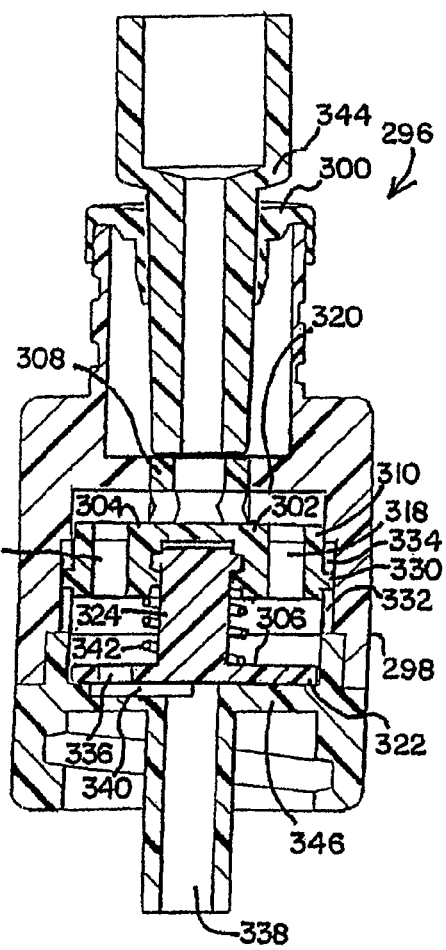

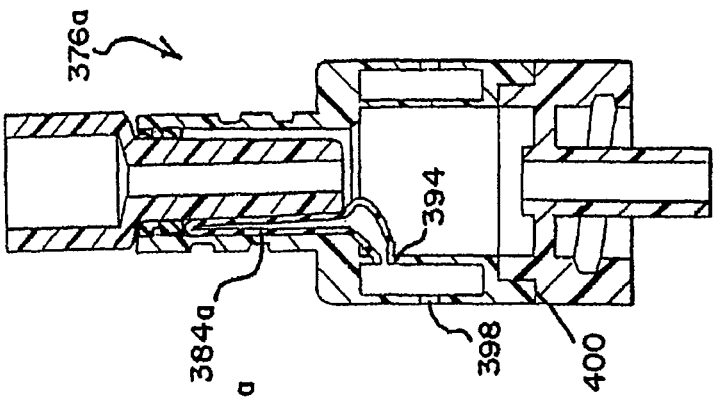
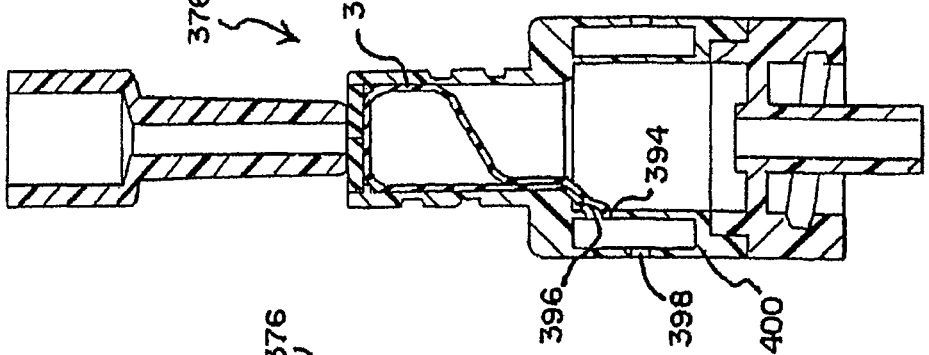
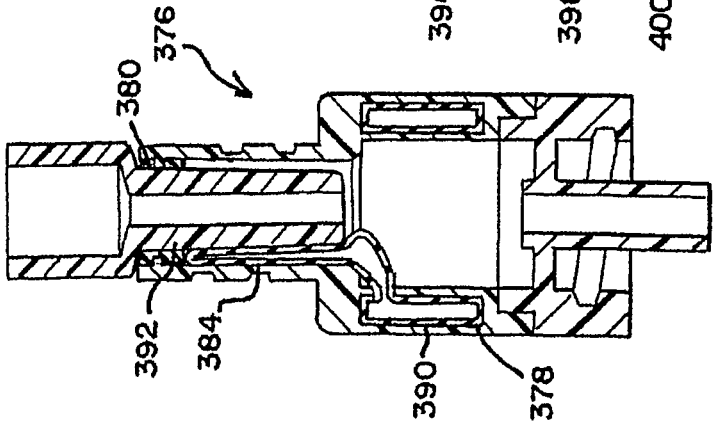
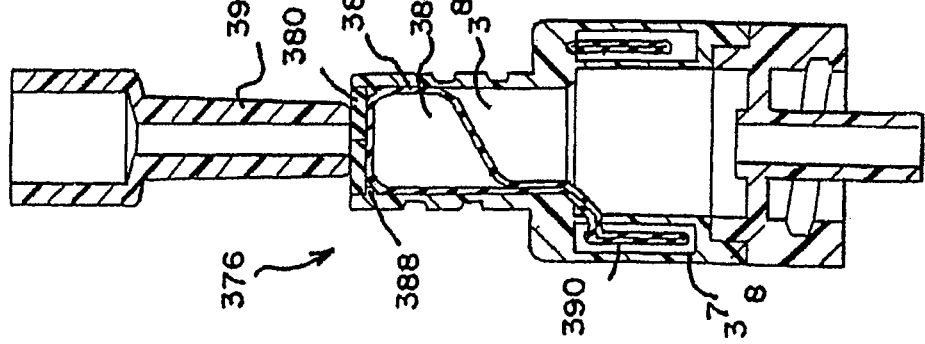

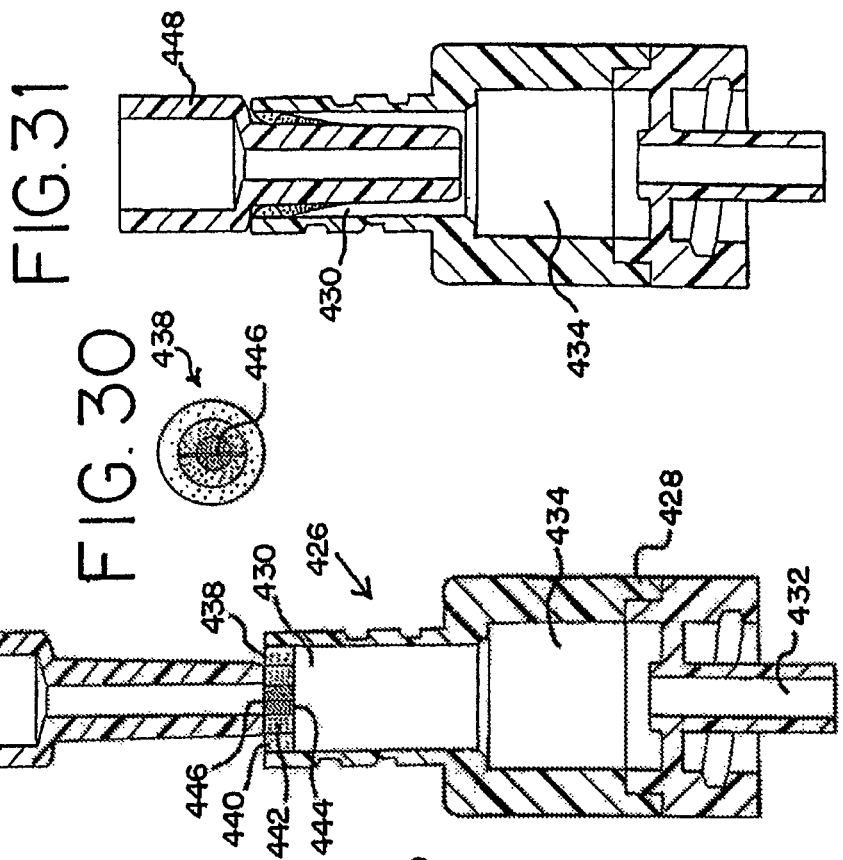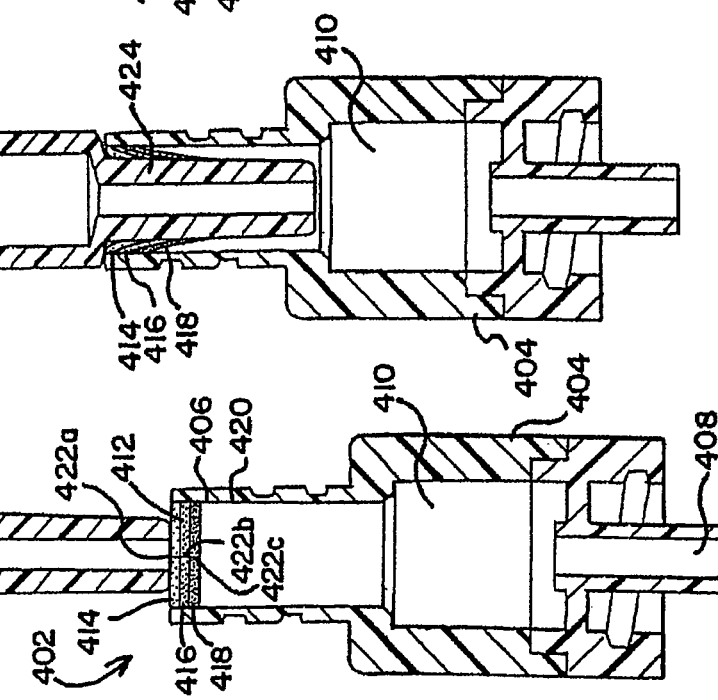

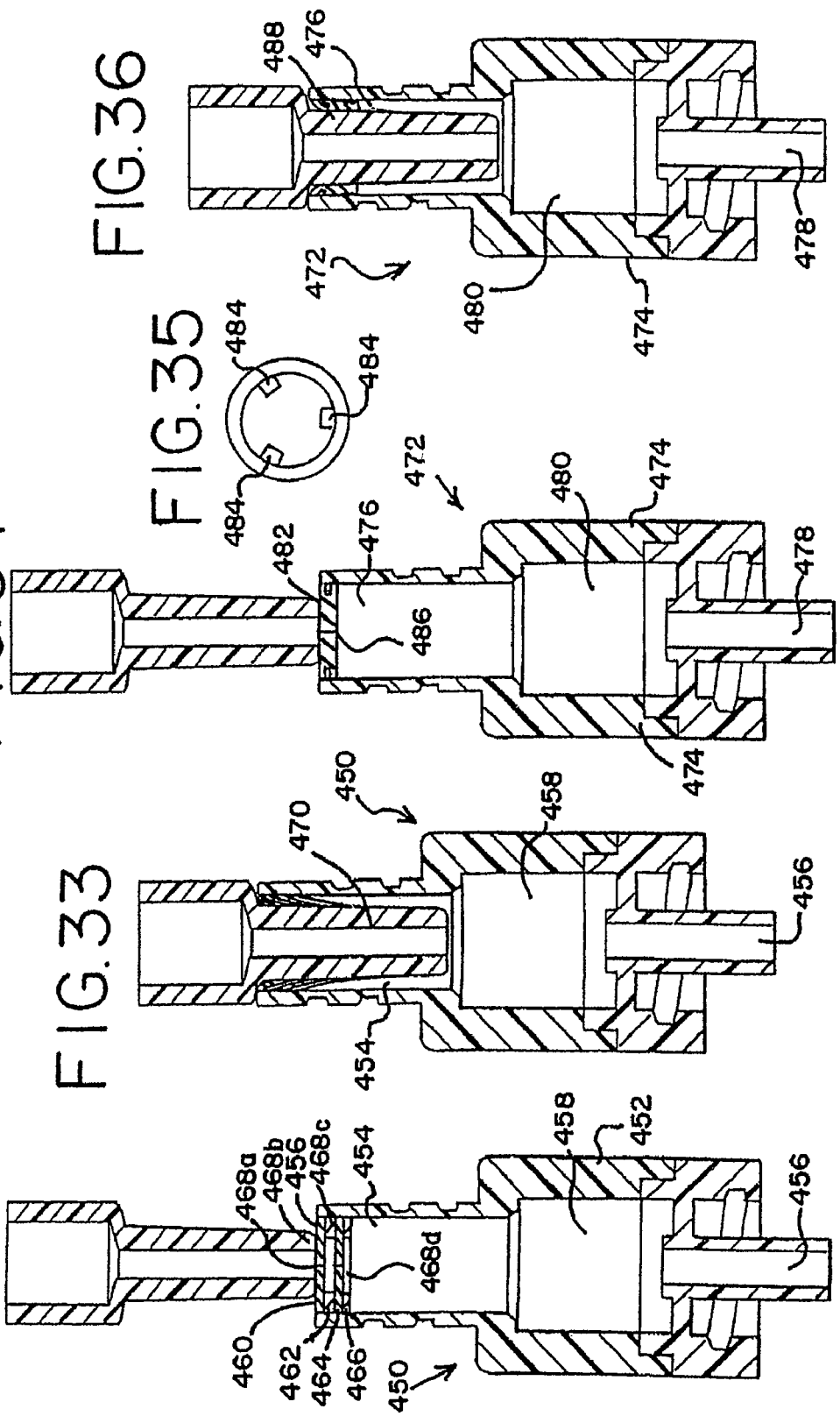

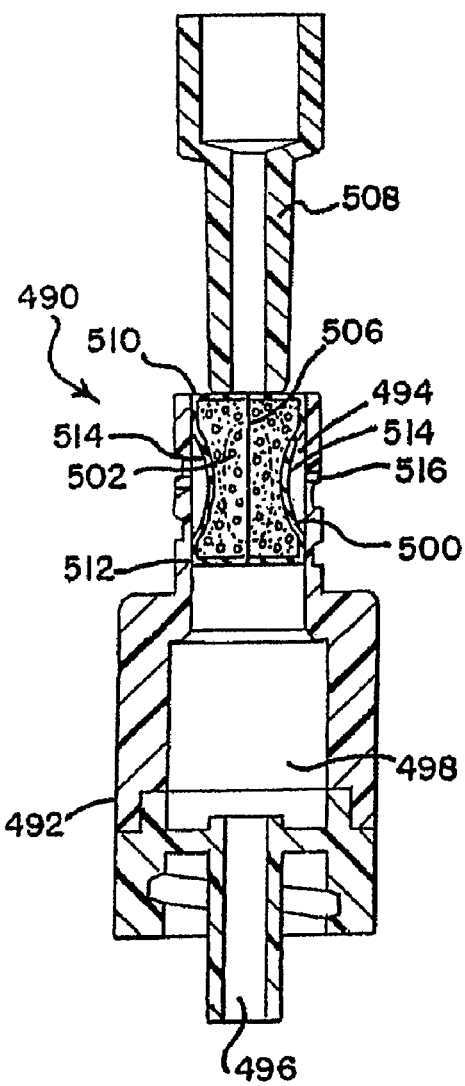
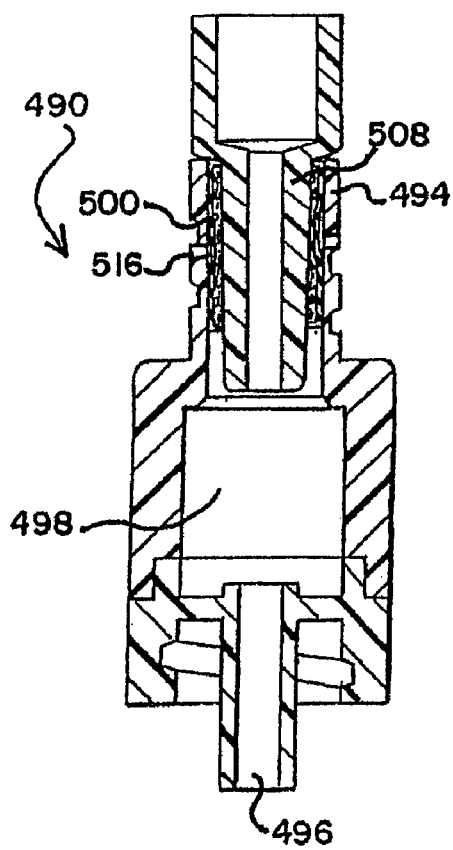
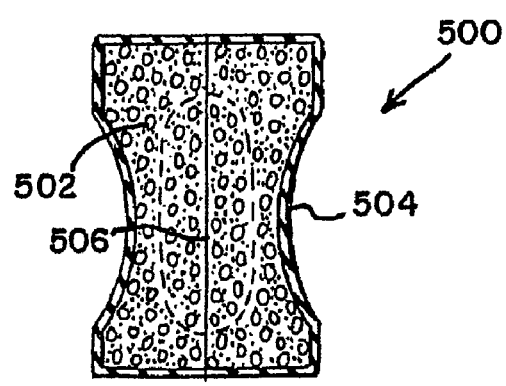

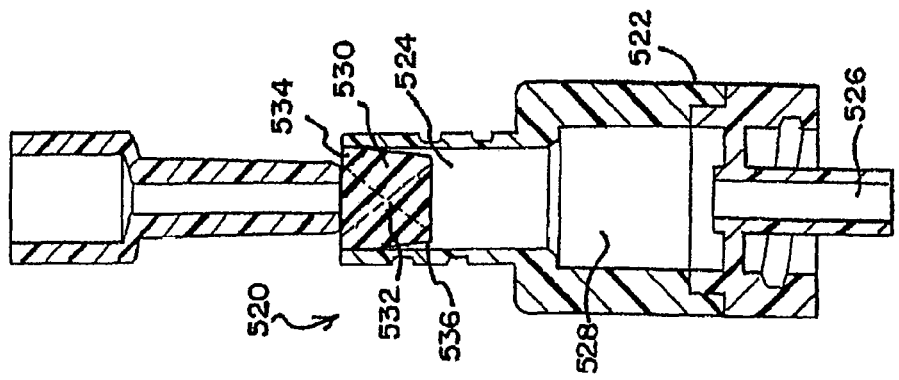
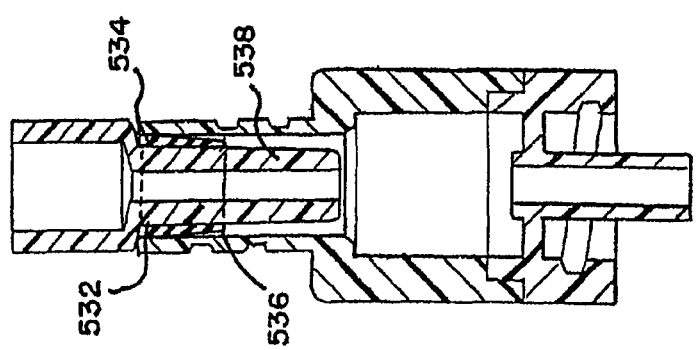
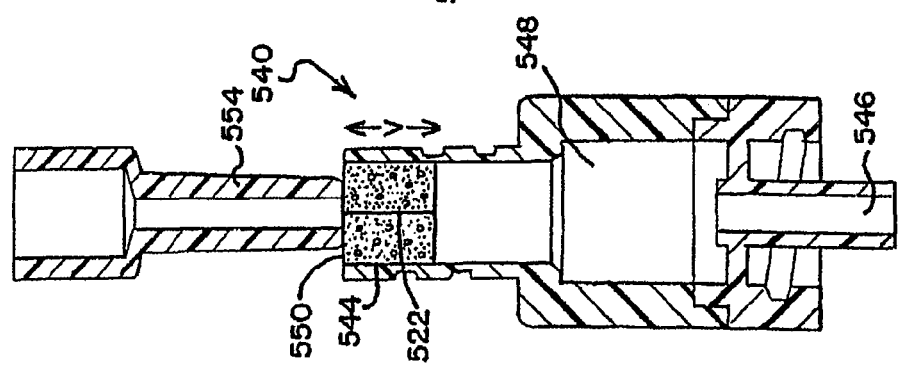
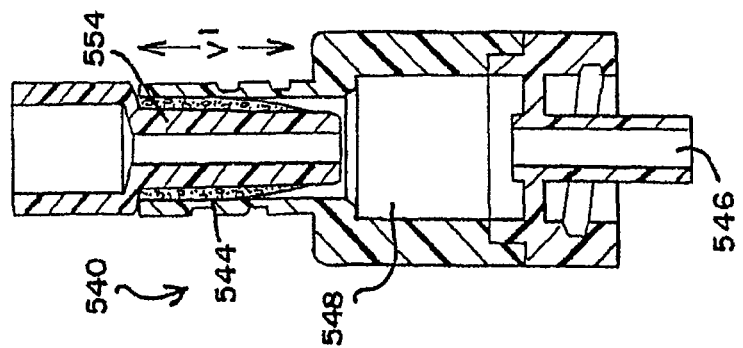

LUER ACTIVATED DEVICE

FIELD OF THE INVENTION

The present invention relates generally to luer activated devices or valves that allow for the bidirectional transfer of fluids to and from medical fluid flow systems.

BACKGROUND OF THE INVENTION

Luer activated devices (LAD) or valves (LAV) are commonly used in association with medical fluid containers and medical fluid flow systems that are connected to patients or other subjects undergoing diagnostic, therapeutic or other medical procedures. A LAD can be attached to or part of a fluid container or a medical fluid flow system to simplify the addition of fluids to or withdrawal of fluids from the fluid flow system.

Within the medical field there are a wide variety of medical fluid flow systems, serving a variety of functions. One of the more common uses of LADs are in association with fluid flow systems that are used for the intravenous administration of fluids, such as saline, antibiotics, or any number of other medically-related fluids, to a patient. These flow systems are commonly referred to as intravenous or "IV" fluid administration sets, and use plastic tubing to connect a phlebotomized subject to one or more medical fluid sources, such as intravenous solution or medicament containers.

Typically, such intravenous administration sets include one or more LADs providing needless access to the fluid flow path to allow fluid to be added to or withdrawn from the IV tubing. The absence of a needle for injecting or withdrawing fluid has the important advantage of reducing the incidence of needle stick injuries to medical personnel. A LAD typically includes a tapered female luer component, such as the inlet into a valve housing, that accepts and mates with a tapered male luer of a medical infusion or aspiration device, such as a needleless syringe or a administration set tubing brand.

There are certain characteristics and qualities of LADs that are highly desirable. For example, the LAD should provide a sufficient microbial barrier for the full service life of the valve. It is desirable that the microbial barrier be conducive to the application of standard aseptic techniques preformed by clinicians during the use of the device. For example, the geometry of the LAD should be such that it is easily swabbable and reduces the potential of entrapping particulates or contaminants that cannot be cleanly swabbed clear prior to use.

Furthermore, it is highly desirable that the LAD be substantially devoid of any interstitial space or any other "dead space" that cannot be flushed, or that such interstitial space be physically isolated from the fluid flow path. Such interstitial space has the potential of providing an environment for undesired microbial growth. In addition, the LAD should have a geometry that allows it to be sufficiently flushed so as to clear the dynamic fluid path and adjacent areas of residual blood or intravenous fluids to prevent undesired clotting.

LAD's are commonly used with intravenous catheters that provide access to a patient's vascular system. In such systems, another desirable feature of a LAD is minimal displacement of fluid during insertion and removal of the male luer. In certain situations, it is preferable that the LAD be a neutral/neutral device in that there is zero or only a very slight displacement of fluid during both insertion and removal of the male luer. In other situations it can be desirable for the LAD to produce a positive displacement of fluid from the valve housing during the removal of the male luer. The LAD also preferably prevents blood reflux into the catheter. Reflux is known to reduce the efficiency of the catheter and also to contribute to catheter clotting.

In most situations it is preferred that the LAD be ergonomically dimensioned to be completely activated by a wide range of ISO compliant male luer lock adaptors. However, there may be some instances when the LAD is specifically designed to be activated by a male luer connector that is not ISO complaint or may not be a luer lock male luer. Another desirable characteristic of a LAD is the ability of the LAD to seal against pressure contained within a fluid system to which the LAD is connected. For example, it is desirable to be leak resistance to positive pressures ranging from 10 to 45 psi and to negative pressures or vacuum from 1 to 5 psi. The LAD also preferably has a geometry that allows for easy priming and flushing that does not require any additional manipulations to remove residual air bubbles from the tubing system.

These and other desirable characteristics, which may be used separately or in combination, is preferably present over the full service life of the valve. When used in connection with an IV set or catheter, the LAD may go through many connections and disconnections. It is desirable that the life of an LAD last through upwards to about 100 connections and disconnections or 96 hours of dwell time.

As described more fully below, the fluid access devices of the present invention provides important advances in the safe and efficient administration or withdrawal of medical fluids to or from a fluid flow system.

SUMMARY OF THE INVENTION

A first aspect of the present invention generally relates to a medical valve for the transfer of fluid. The medical valve comprises a housing having an inlet, an outlet and a flow path defined therebetween. The medical valve also includes a first valve associated with the inlet wherein the first valve is adapted for receiving a male luer therethrough. In a further embodiment the medical valve further a second valve normally substantially sealing said flow path distal to said first valve. The second valve is movable to open flow through the flow path by the action of the insertion of a male luer into the inlet.

Another aspect of the present invention generally relates to a medical valve for the transfer of fluid. The medical valve comprises a housing having an inlet, an outlet and a flow path defined therebetween. The medical valve also includes a valve associated with the housing wherein the valve includes a plurality of layers, each layer comprising a material having desired characteristics. The valve further includes an aperture for receiving a male luer.

Yet another aspect of the present invention generally relates to a medical valve for the transfer of fluid. The medical valve comprises a housing having an inlet, an outlet and a flow path defined therebetween. The medical valve also includes a valve associated with the housing wherein the valve includes a plurality of annular segments and an aperture for receiving a male luer.

A further aspect of the invention generally relates to a medical valve for the transfer of fluid. The medical valve includes a housing having an inlet, an outlet and a flow path defined therebetween. The medical valve also includes a valve associated with the housing wherein the valve comprises a septum that includes an aperture and at least one biasing member to bias the septum to a position in which the aperture is closed.

Another aspect of the invention generally relates to a medical valve for the transfer of fluid. The medical valve includes a housing having an inlet, an outlet and a flow path defined therebetween. The medical valve also includes a valve associated with the housing wherein the valve comprises a plurality of discrete particles that are free to move in relation to one another to accommodate the insertion of a male luer through the valve inlet.

Another aspect of the invention generally relates to a medical valve for the transfer of fluid. The medical valve includes a housing having an inlet, an outlet and a flow path defined therebetween. The medical valve also includes a valve associated with the housing wherein the valve comprises a septum having a slit that varies directionally with slit extent through the septum.

Another aspect of the invention generally relates to a medical valve for the transfer of fluid. The medical valve includes a housing having an inlet, an outlet and a flow path defined therebetween. The medical valve also includes a valve associated with the housing wherein the valve comprises a first portion and a second portion in which the second portion is rotatable relative to the first portion. The valve also has an aperture through the valve. The aperture is disposed to cause rotation of the second portion relative to the first portion upon insertion of a male luer therethrough.

Another aspect of the invention generally relates to a medical valve for the transfer of fluid. The medical valve includes a housing having an inlet, an outlet and a flow path defined therebetween. The medical valve also includes a valve associated with the housing wherein the valve comprises a first portion generally rotationally fixed relative to the housing and a second portion proximal or distal of the first portion and rotatable relative to the housing.

Another aspect of the invention generally relates to a medical valve for the transfer of fluid. The medical valve includes a housing having an inlet, an outlet and a flow path defined therebetween. The medical valve also includes a valve associated with the housing wherein the valve comprises a valve element located within the flow path of the valve housing. The valve element is movable from a first position to a second position by contact with a male luer inserted into the valve housing inlet. The valve element prevents fluid flow through the flow path when the valve element is in the first position, and permits fluid flow through the flow path when in the second position. The valve element is biased to the first position and returns to the first position upon removal of the male luer from the housing.

Another aspect of the invention generally relates to a medical valve for the transfer of fluid. The medical valve includes a housing having an inlet, an outlet and a flow path defined therebetween. The medical valve includes a valve associated with the housing wherein the valve has a proximal end portion, a distal end portion and a fluid passageway extending therethrough. The distal end portion of the valve defines a normally closed fluid passageway opening and a rigid actuator disposed in the valve. The actuator is operable upon contact with a male luer to open the fluid passageway opening.

Another aspect of the invention generally relates to a medical valve for the transfer of fluid. The medical valve includes a housing having an inlet, an outlet and a flow path defined therebetween. The medical valve includes a valve associated with the housing wherein the valve has a proximal end and a distal end and a fluid passageway extending therethrough. The distal end comprises a plurality of movable elements defining an opening to the fluid passageway and the movable elements are biased to a closed position.

Another aspect of the invention generally relates to a medical valve for the transfer of fluid. The medical valve includes a housing having an inlet, an outlet and a flow path defined therebetween. The medical valve also includes a valve associated with the housing wherein the valve comprises a first position in which the valve prevents fluid flow through the medical valve and a second position in which the valve allows fluid flow through the medical valve. The valve is biased to the first position.

Another aspect of the invention generally relates to a medical valve for the transfer of fluid. The medical valve includes a housing having an inlet, an outlet and a flow path defined therebetween. The medical valve also includes a valve having a rotatable fluid flow control member that generally rotates about the axis of the medical valve. The fluid control member has a first position in which the fluid flow control member prevents the flow of fluid through the medical valve and a second position in which the fluid flow control member permits the flow of fluid through the medical valve.

Another aspect of the invention generally relates to a medical valve for the transfer of fluid. The medical valve includes a housing having an inlet, an outlet and a flow path defined therebetween. The medical valve also includes a valve associated with the housing wherein the valve comprises a rotatable member that rotates along an axis that is generally transverse to a central axis of the valve housing. The rotatable member having a first position in which it blocks fluid flow through the medical valve and a second position in which it allows fluid flow through the medical valve. The rotatable member movable between the first position and the second position by contact with the male luer inserted into the housing.

Another aspect of the invention generally relates to a medical valve for the transfer of fluid. The medical valve includes a housing having an inlet, an outlet and a flow path defined therebetween. The medical valve also includes a valve associated with the housing wherein the valve comprises a fluid chamber that creates a seal with the inlet of the valve housing. The fluid chamber is compressible to accommodate the insertion of a male luer with a minimum displacement of fluid through the outlet of the valve housing when the male luer is inserted into the valve housing.

BRIEF DESCRIPTION OF THE DRAWINGS

Turning now to a more detailed description of the various embodiments of the present invention illustrated in the attached drawings, of which:

FIG. 1 is a cross-sectional view of one embodiment of a luer activated device of the present invention;

FIG. 2 is a cross-sectional view of the LAD of FIG. 1, shown engaged with a male luer;

FIG. 3 is a cross-sectional view of the LAD of FIG. 1, shown with the male luer being retracted from the LAD;

FIG. 4 is a perspective view of one of the valves of the LAD of FIG. 1;

FIG. 5 is a cross-sectional view of another embodiment of a LAD of the present invention;

FIG. 6 is a cross-sectional view of the LAD of FIG. 5, shown engaged with a male luer;

FIG. 7 is a perspective view of one of the valves of the LAD of FIG. 5;

FIG. 8 is a perspective view of an alternative embodiment of the valve of FIG. 7;

FIG. 9 is a cross-sectional view of another embodiment of the LAD of the present invention;

FIG. 10 is a cross-sectional view of the LAD of FIG. 9, shown engaged with a male luer;

FIG. 11 is a perspective view of one embodiment of one of the valves of the LAD of FIG. 9, shown in a non-actuated configuration;

FIG. 12 is a perspective view of the valve of FIG. 11, shown in an actuated configuration;

FIG. 13 is a cross-sectional view of an alternative embodiment of the valve of FIGS. 11-12;

FIG. 18 is a cross-sectional view of another embodiment of a LAD of the present invention;

FIG. 19 is a cross-sectional view of the LAD of FIG. 18, shown engaged with a male luer;

FIG. 23 is a cross-sectional view of another embodiment of a LAD of the present invention;

FIG. 24 is a cross-sectional view of the LAD of FIG. 23, shown engaged with a male luer;

FIG. 25 is a cross-sectional view of another embodiment of a LAD of the present invention;

FIG. 26 is a cross-sectional view of the LAD of FIG. 25, shown engaged with a male luer;

FIG. 27 is a cross-sectional view of another embodiment of a LAD of the present invention;

FIG. 28 is a cross-sectional view of the LAD of FIG. 27, shown engaged with a male luer;

FIG. 29 is a cross-sectional view of another embodiment of a LAD of the present invention;

FIG. 30 is a top view of the valve member of the LAD of FIG. 29;

FIG. 31 is a cross-sectional view of the LAD of FIG. 29, shown engaged with a male luer;

FIG. 32 is a cross-sectional view of another embodiment of a LAD of the present invention;

FIG. 33 is a cross-sectional view of the LAD of FIG. 32, shown engaged with a male luer;

FIG. 34 is a cross-sectional view of another embodiment of a LAD of the present invention;

FIG. 35 is a top view of the housing of the LAD of FIG. 34, shown without the valve;

FIG. 36 is a cross-sectional view of the LAD of FIG. 34, shown engaged with a male luer;

FIG. 37 is a cross-sectional view of another embodiment of a LAD of the present invention;

FIG. 38 is a cross-sectional view of the valve of the LAD of FIG. 37;

FIG. 39 is a cross-sectional view of the LAD of FIG. 37, shown engaged with a male luer;

FIG. 40 is a cross-sectional view of another embodiment of a LAD of the present invention;

FIG. 41 is a cross-sectional view of the LAD of FIG. 40, shown engaged with a male luer;

FIG. 42 is a cross-sectional view of another embodiment of a LAD of the present invention; and FIG. 43 is a cross-sectional view of the LAD of FIG. 42, shown engaged with a male luer.

DETAILED DESCRIPTION OF THE INVENTION

Figure 14:
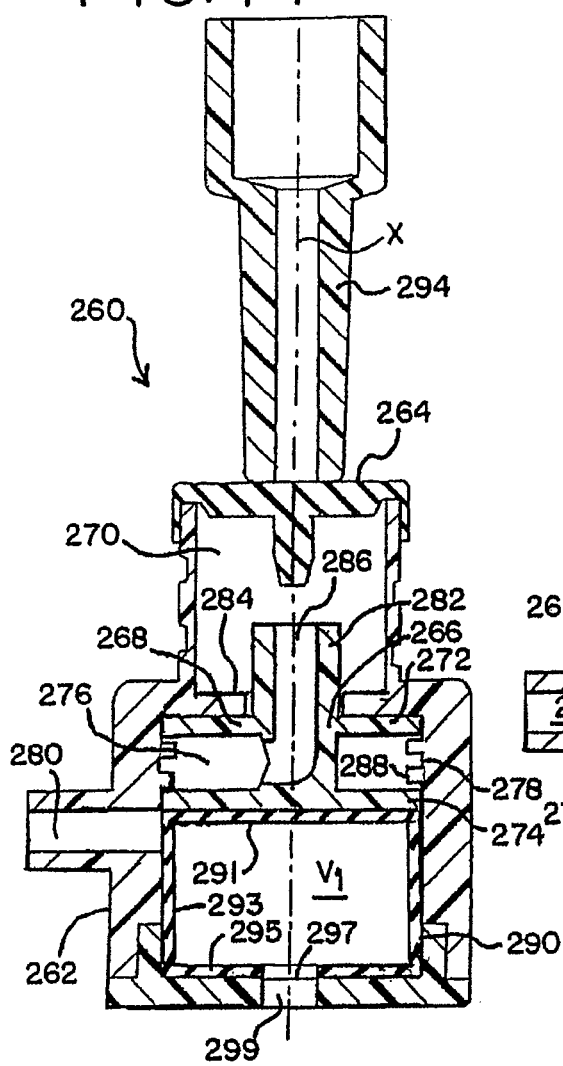
FIG. 14 is a cross-sectional view of another embodiment of a LAD of the present invention.

Detailed embodiments of the present invention are disclosed herein for exemplary purposes only, and it is to be understood that the present invention may be embodied in various forms. Therefore, specific details disclosed herein are not to be interpreted as limiting, but as a representative basis for teaching one skilled in the art to variously employ the present invention in virtually any appropriate manner.

The following illustrated embodiments of the luer activated devices are described as employing various valves. The terms "upper valve" or "first valve" and "lower valve" or "second valve" are not intended to be limiting, and such designations are used solely for convenience to describe the location of the valve in a particular embodiment. It should be understood that the valves disclosed herein, for addition or withdrawal of fluids and can be used alone or in conjunction with other valves and valve elements.

FIGS. 1-4 generally illustrate one embodiment of a luer activated device (LAD) of the present invention, generally designated as 110. The LAD 110 includes a housing 112 comprised of a rigid material, such as plastic or other suitable material. The housing 112 preferably includes an upper housing 114 and a lower housing 116 that can be joined together, for example, by welding. The upper housing 114 includes an inlet 118, and the lower housing 116 includes an outlet 120. A fluid flow path 122 is defined by an internal wall 115 of the housing 112 and extends between the inlet 118 and the outlet 120. The terms "inlet" and "outlet" are not to be interpreted as limiting the LADs disclosed herein to applications involving fluid flow in a particular direction, e.g., from the inlet to the outlet, because LADs according to the present invention may be used in applications involving fluid flow from the inlet to the outlet or from the outlet to the inlet.

An internal wall 117 of the inlet 118 is preferably sized and configured to conform with ISO and ANSI standards and is designed to receive a variety of male luers that conform to ISO and ANSI standards. Alternatively, the inlet 118 can also be configured to receive male luers or other medical implements that do not conform to any particular standard. Preferably, the internal wall 117 has a taper which corresponds to the standard taper of a male luer. In the illustrated embodiment, the inlet may include external threads 119 adapted to removably lock with a collar of a male luer (not shown). The outlet 120, which may be in the form of a male luer, a female luer or other attachment configuration, can be connected to any number of fluid flow systems or medical fluid containers. For, example the LAD 110 can be connected to an IV administrative tubing set that engages internal threads 121 of collar 123. Alternatively, the LAD can be an integral part of a larger device.

The LAD 110 preferably includes an upper or first valve 124 and a lower or second valve 126. The first valve 124 seals the inlet 118 of the upper housing 114. A variety of valve configurations are disclosed herein, and it should be noted that the first valve 124 may be any of the valves disclosed herein (see, FIGS. 27-43) or could be any other valve known in the art, for example the valve disclosed in U.S. Pat. No. 6,344,033 to Jepson et al., filed Aug. 9, 1999 and hereby incorporated herein by reference. In one embodiment, the first valve 124 is an elastic resealable member, such as septum 128, made of natural latex, silicone or some other elastic polymeric material. In the embodiment illustrated in FIG. 1, the septum 128 is attached to the upper housing 114 by a curtain 130 that extends around a rim 132 of the inlet 118. The curtain 130 can be attached to the rim 132 by adhesive bonding or by any other method known in the art, such as overmolding. The septum 128 provides a microbial barrier between the internal fluid flow path 122 of the LAD and the atmosphere. The septum 128 preferably includes a substantially flat upper surface 134 that can be easily wiped with antiseptic and has a geometry that discourages any particulates from becoming trapped on the upper surface. The upper surface 134 of the septum may also include an antimicrobial coating, or the material of the septum 128 can be impregnated with an antimicrobial agent to enhance antimicrobial protection. For male luer access into the LAD, the septum 128 also preferably includes a resealable aperture, which may be in the form of a resealable slit 136, for receiving a male luer therethough, and allowing the male luer to access the fluid flow path 122 of the LAD and activate the second valve 126. The slit 136 maybe formed using several techniques including slitting after molding as well as being formed during molding. When the male luer is inserted through the slit 136, the slit deforms and preferably the septum presses against the male luer to form a seal that prevents leakage from the inlet 118.

The second valve 126 is located in the flow path 122 at a location below or distal the first valve 124. The second valve normally closes the fluid flow path 120 until actuated by insertion of or flow of fluid from a male luer inserted into the LAD. The second valve 126 may be a variety of valves having a variety of features or characteristics, depending on the desired application. In the embodiments illustrated in FIGS. 1-4, for example, the second valve 126 includes a valve element or plug 138 that reciprocates between a normally closed position (FIG. 1), which prevents fluid flow through the flow path 122, and an open position (FIG. 2), which permits fluid flow through the flow path 122. As illustrated in FIGS. 1-3, the valve element 138 is biased to the closed position by a biasing member, such as the illustrated spring 140. The biasing member could also be any other biasing member known in the art, such as a compressible chamber or an element in tension. The spring 140 is preferably comprised of a biocompatible metal or polymer. In certain applications, such as when the LAD is employed in an MRI setting, it is desirable for the spring 140 or other biasing member to be comprised of a non-ferromagnetic material. When the biasing member is a helical spring, as illustrated, the valve element 138 can include a lower portion 142, which extends into and resides within the spring 140 to provide stability of the connection between the valve element 138 and the spring 140.

The illustrated valve element 138 also includes an upper portion 144 that extends slightly into the throat 146 of the LAD 110 when the plug is in the closed position. The engagement between the upper portion 144 of the valve element 138 and the throat 146 aids in guiding and maintaining the valve element 138 in the proper position as the plug moves between the open and closed positions. In the closed position, a radially extending sealing surface, such as shoulder 148, of the valve element 138 contacts a valve seat of the housing, for example, a circumferential sealing shoulder 150 of the housing 112, to form a fluid tight seal that resists back pressure that may be built-up within the fluid system.

In operation, referring to FIG. 2, a male luer 152 is inserted into and through the slit 136 of the septum 128. The male luer 152 enters the flow path 122 and comes into contact with protrusions or stand-offs 154 located on the upper portion 144 of the valve element 138. As the male luer 152 is advanced further into the LAD 110, it pushes against the valve element 138 and forces the valve element in a downward direction toward the outlet 120. As the valve element 138 moves downward, the sealing shoulder 148 of the valve element 138 moves out of engagement with the shoulder 150 the housing 112. The valve element 138 moves in a downward direction until the upper portion 144 of the plug is below the sealing shoulder 150 of the housing 112, creating a fluid flow path between the valve housing 112 and the plug 138. Optionally, fluid flow channels can be located in a wall of the housing 112 to increase the flow rate through the LAD when the valve element 138 is in the actuated position. The stand-offs 154 (FIG. 4) prevent the male luer 152 from occluding during fluid delivery or withdrawal, and provide fluid paths 156 for the flow of fluid into and out of the male luer. In the fully actuated position, fluids can be infused into or aspirated from the fluid system through the LAD.

Referring to FIG. 3, as the male luer 152 is withdrawn from the LAD 110, the spring 140 biases the valve element 138 to return to its closed position. An occluding surface, such as occluding shoulder 158 of the upper portion 144 of the valve element, forms an initial occlusion with the throat 146 of the housing as the valve element moves upwardly. As illustrated, the occlusion can be a restricted flow path between the occluding shoulder 158 and the throat 146 or an actual sealing contact. The size of the restricted flow path can depend on tolerances in manufacturing and is preferably a gap about 0.01 (0.25 mm) or less inches between the occluding shoulder 158 and the throat 146. Alternatively, the occluding shoulder 158 can contact the throat 146 to create the occlusion. After shoulder 158 of the valve element 138 forms a fluid occlusion with the throat 146 of the housing, the fluid located downstream of the occlusion in the space 160 between the sealing shoulder 148 of the valve element 138 and sealing shoulder 150 of housing 112 is prevented by the occlusion from flowing toward the inlet 118 and is pushed toward the outlet 120 of the valve housing 112 as the sealing shoulder 148 moves into engagement with sealing shoulder 150. This push creates a positive displacement of fluid toward the valve outlet 120. This positive displacement can create an overall positive displacement or a substantially neutral displacement depending on the dimensions of the plug and the plug housing.

Furthermore, it will be understood by those of ordinary skill that when a male luer is removed from a LAD having a septum as its only valve, that the removal of the male luer tends to draw fluid into the LAD through the outlet. In other words, the slight pressure drop caused by withdrawal of the male luer results in undesirable reflux into the outlet from the fluid system. In contrast, in the LAD 110 of FIGS. 1-3, as the male luer 152 is initially withdrawn, the valve element 138 first preferably occludes via the occluding shoulder 158 and then fully seats with the valve seat of the housing 112 before the male luer is substantially withdrawn from the LAD. As soon as the valve element 138 is seated, the inlet 118 is out of communication with the valve outlet 120, and the further removal of the male luer 152 or creation of a vacuum in the upper housing 114 will not have any net effect on the displacement of fluid into or out of the valve outlet 120—substantially preventing reflux into the valve housing 112.

FIGS. 5-8 illustrate another embodiment of a LAD of the present invention, generally designated 162. Referring to FIG. 5, LAD 162 has generally the same features as the LAD of the previous embodiment, including an occluding shoulder. However, in this embodiment, the radially extending sealing shoulder 164 of the valve element 166 is thicker and the circumference of the sealing shoulder is such so that the distance between the sealing shoulder 164 and inner surface 165 of the housing 168 is shorter than in the previous embodiment. This smaller distance between the sealing shoulder 164 and the inner surface 165 of the housing 168 aids in guiding and maintaining the alignment of the valve element 166 as the element reciprocates between the open position and the closed position.

Referring to FIGS. 5-7, the plug 166 includes fluid flow passageways 170 that allow the passage of fluid through the plug 166 when the plug is in the open position. In order to prevent a flow restriction of the fluid transferred to and from the male luer and to enhance the flow rate through the valve, it is preferable that the sum of the areas of the openings of the fluid flow passageways 170 is equal to or greater than the area of the opening 171 of the tip 172 of the male luer 174.

In the closed position, the plug sealing shoulder 164 is biased against a shoulder 176 of the housing and the fluid flow passageways 170 are seated against the shoulder 176 of the housing to close off the fluid flow passages and form a fluid tight seal, as illustrated in FIG. 5. Referring to FIG. 7, when the male luer is inserted into the LAD 162 and contacts the raised stand-offs on the valve element 166, the valve element is moved away from the sealing shoulder 176 of the housing 168 and fluid is permitted to flow through the fluid flow passageways 170. FIG. 8 illustrates an alternative embodiment of the plug 166a in which the fluid flow passageways 170a are defined by grooves 178 located at the edge 180 of the sealing shoulder 164a of the valve element 166a. The valve element 166 operates similar to FIGS. 1-4 when the male luer is withdrawn. Occluding shoulder or area 179 contacts or forms an occluding gap with housing shoulder 181 to create an initial occlusion that aids in preventing reflux and in creating a positive pressure pulse through the outlet if desired.

FIGS. 9-10 illustrate another embodiment of a LAD of the present invention, generally designated as 182. The LAD 182 includes a housing 184 that is generally similar to the housings of the previous embodiments and includes a first valve 186 and a second valve 188. The first valve 186 is generally similar to the first valve elements of the previous embodiments and, for example, can be any septum or other suitable type of valve element generally known in the art or described herein.

The second valve 188 is comprised of valve element 190 that is located in the fluid pathway 192 of the valve housing 184. The valve element 190 is preferably made from latex or from an elastic polymeric material, such as silicone, and has a top portion 194, a middle disc shaped portion 196 and a bottom frusto-conical portion 198. A passageway 200 extends from the top portion 194 to the bottom portion 198. The valve element 190 can be secured to the housing 184 by securing the middle disc shaped portion 196 between the upper housing 202 and the lower housing 204. Preferably, the middle portion is mounted with a radially directed compression. Alternatively, the valve element 190 can be secured to the housing by some other means, such as adhesive bonding.

The bottom frusto-conical portion 198 is divided into a plurality of valve elements or prongs 206 that can be formed during molding of the valve element 190 or can be formed by slitting the valve element after molding. In the illustrated embodiment, the bottom frusto-conical portion 198 is divided into three pie-shaped elements or prongs 206. The prongs 206 are movable between an open position in which fluid flow is permitted through the LAD 182, and a closed position in which fluid is prevented from flowing through the LAD 182. In the closed position, the prongs 206 engage each other to close off the passageway 200 at the bottom of the resilient member, as illustrated in FIGS. 9 and 11. In the open position, the prongs 206 move in a radially outward direction and separate to open the passageway 200 in the valve element 190, as illustrated in FIGS. 10 and 12. Preferably, the prongs 206 are normally biased to the closed position by the resiliency of the material of the valve element 190. Additionally, the radial tension exerted on the middle disc shaped portion 196 between the upper and lower housings 202, 204 can also aid in biasing the prongs 206 to the closed position. In an alternative embodiment, referring to FIG. 13, at least one biasing member 205 can be placed around the frusto-conical bottom portion 198 of the resilient member to compress the prongs 206 to the closed position. The biasing member 205 can be a rubber band-like element that is held to a groove 207 located in the bottom portion 198 of the resilient member 190, or other biasing structure.

To actuate the valve element 190, a rigid member, preferably tubular member 208, is disposed within internal passageway 200 of the valve element 190. The tubular member includes a lower portion 210, which is disposed within passageway 200 of the valve element 190, and an upper portion 212, which extends upwardly from the valve element 190 into the fluid pathway 192 of the housing 184 for engagement by a male luer inserted into the LAD. The tubular member 208 can be secured to the valve element 190 by an interference fit between an annular radial projection 214 projecting from the lower portion 210 of the tubular member 208 and a corresponding groove or cavity 216 in the bottom portion 198 of the valve element 190. Alternatively, the tubular member 208 can be secured to the valve element 190 by any suitable methods know in the art, such as adhesive bonding.

FIG. 10 shows a male luer 216 received through the first valve 186 into the valve housing 184. In the valve housing, the male luer 216 engages the upper portion 212 of the tubular member 208 so that the opening 218 of the male luer tip 220 generally aligns with the passageway 222 through the tubular member 208. The tubular member 208 may include stand-offs (not shown), so that the male luer is in fluid communication with the space 224 between the first valve 186 and the second valve 188. The male luer is preferably in fluid communication with space 224 so that any fluid within this space does not become stagnant, and such space 224 is easily flushable during the use of the LAD. As the male luer 216 is inserted further into the LAD, the male luer 216 places a downward force on the tubular member 208 which moves the tubular member in a downward or distal direction, placing a downward pressure on the bottom portion 198 of the valve element 190. The downward pressure on the bottom portion 198 of the valve element 190 causes the prongs 206 to separate and move radially into the open configuration, thereby allowing fluid to flow through the tubular member 208 and the valve element 190. After the desired amount of fluid has been infused or aspirated, the male luer 216 is withdrawn from the housing 184 and the first and second valve elements 186, 188 return to their normally closed positions.

Similar to the previous embodiments in FIGS. 1-3, as the male luer 216 is initially withdrawn from the LAD 182, the prongs 206 almost immediately engage to close valve element 190. Upon the closure of the valve element 190, the space 224 between the first valve 186 and second valve 188 is out of fluid communication with the valve outlet 215. Because of the lack of fluid communication between the 224 and the valve outlet 215 further removal of the male luer 216 from the LAD 182 will not have any net effect on the displacement of fluid from the outlet 216—thereby reducing reflux.

FIGS. 14-17 illustrate another embodiment of a LAD of the present invention, generally designated 260. The LAD 260 includes a housing 262, a first valve 264 and a second valve 266. The first valve 264 is generally similar to the first valve of the previous embodiments and, for example, can be any suitable septum or other type valve element generally known in the art or described herein.

Figure 15:
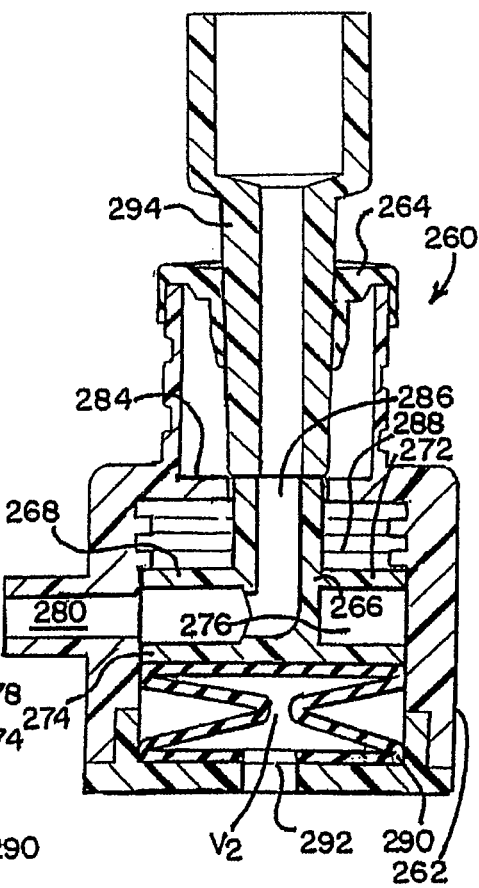
FIG. 15 is a cross-sectional view of the LAD of FIG. 14, shown engaged with a male luer.
Figure 16:
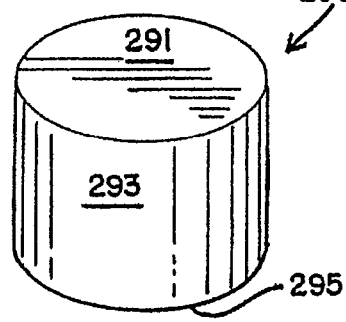
FIG. 16 is a perspective view of the biasing member of the LAD of FIG. 14, shown in the non-actuated configuration.

The second valve 266 includes a valve element or piston 268 that reciprocates along a central axis "x" of the valve housing 262 between a non-actuated position (FIG. 14) and an actuated position (FIG. 15). The central axis of the valve, as illustrated, is the axis that passes through the inlet 270 of the valve housing, although other arrangements may also be feasible. The valve 268 has an upper disc member 272 and a lower disc member 274 defining a space 276 therebetween. When the piston 268 is in the non-actuated position (FIG. 14), the space 276 between the upper disc 272 and the lower disc 274 is contained by the internal walls 278 of the housing 262 and is spaced from and out of fluid communication with valve outlet 280 located in the side of the housing 262. When the valve element 268 is in the actuated position (FIG. 15), the space 276 between the upper disc 272 and the lower disc 274 is in fluid communication with the valve outlet 280.

A tubular member 282 extends from the upper disc member 272 through a neck portion 284 located within the housing 262. The tubular member 282 includes a fluid flow passageway 286 that communicates with the space 276 defined by the upper disc member 272 and lower disc member 274. When the valve element 268 is in the actuated position, the passageway 286 of the tubular member 282 is in communication with the valve outlet 280 via space 276.

In accordance with another aspect, the upper disc member 272 of the piston 268 may engage threads 288 that are located in the internal wall 278 of the valve housing 262 so that when the piston 268 reciprocates in the valve housing 262, the disc member 272 follows along the threads 288 resulting in rotational movement of the piston 268 about the central axis of the valve housing 262. As illustrated, the piston 268 is biased to the non-actuated position by a compressible air chamber 290. As may be seen in FIGS. 14 and 16, in the non-actuated position the chamber 290 may have a generally cylindrical configuration, with a top wall 291, a circumferential sidewall 293 and a bottom wall 295. The top wall 291 may be secured to the lower disc member 274 of the piston 268. There is an annular gap formed between the sidewall 293 and the housing 262. In an embodiment the gap is approximately 1 mm to 2 mm.

Figure 17:
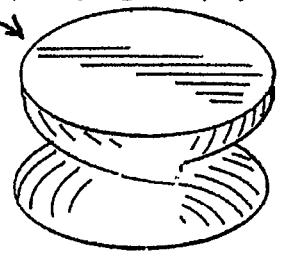
FIG. 17 is a perspective view of the biasing member of FIG. 16, shown in the actuated configuration.

Accordingly, as the valve element 268 is moved to the actuated position and rotates about the central axis, the air chamber 290, which is connected to the lower disc member 274, compresses onto itself in a twisting sidewall 293, as illustrated in FIG. 17. The air chamber 290 is vented through a vent 292 in the bottom wall 295 of air chamber 290 and vent 297 in the bottom wall 299 of the valve housing 262 to expel air from the air chamber 290 as the chamber is compressed.

In the non-actuated position, the air chamber 290 has a volume $V_1$ and in the actuated position, the compressed air chamber has a volume $V_2$, which is less than volume $V_1$. Preferably, the change in volume of the air chamber 290 from $V_1$ to $V_2$ is equal to the volume of the portion of the male luer 294 entering the valve housing 268. In addition fluid may flow into the annular gap between the sidewall 293 and housing 262.

Referring to FIG. 15, in use, the male luer 294 is inserted through the first valve 264 and into the valve housing 262. In the valve housing 262, the male luer 294 engages the tubular member 282 and pushes the valve element 268 in a downward direction. As the valve element 268 moves downward in valve housing 262, the valve element 268 rotates about the central axis causing the air chamber 290 to compress onto itself by a twisting of sidewall 293. The valve element 268 moves downward until the space 276 is in communication with the outlet 280 and vice versa. In this fully actuated position, fluid can be transferred from the male luer 294 to the valve outlet 280 and fluid flows into the annular gap.

After the desired amount of fluid is transferred, the male luer 294 is removed from the housing 262 and the air chamber 290 biases the piston 268 back into the non-actuated position. Because the male luer needs to be withdrawn only a small distance before the space 276 is out of communication with outlet and fluid is forced out of the annular gap, reflux into the LAD is limited or there may actually be a positive displacement of fluid through the outlet.

FIGS. 18 and 19 illustrate another embodiment of a LAD of the present invention, generally designated 296. The LAD 296 includes a housing 298 that is generally similar to the housings of the previous embodiments and includes a first valve 300 and a second valve 302. The first valve 300 is generally similar to the first valve elements of the previous embodiments and, for example, can be any suitable septum or other type of valve element generally known in the art or described herein.

The second valve 302 includes a piston 304 rotatably connected to a rotatable member 306. The piston 304 reciprocates in the valve housing 298 and has a non-actuated position (FIG. 18) and an actuated position (FIG. 19). The piston 306 includes an upper portion 308 and a lower portion 310. The upper portion 308 of the piston extends through a neck 312 in the housing 298 and has fluid flow paths 314 which are sealed by a portion 316 of the neck 312 when the piston 304 is in the non-actuated position. The lower portion 310 of the piston 304 also includes fluid pathways 318 that are sealed by a lower surface 320 of the neck 312 when the piston 304 is in the non-actuated position.

The rotatable member 306 includes a base 322 and an upward extending portion 324. The upward extending portion 324 includes a cam follower or projection 326 that engages a cam track or threads 328 located in the lower portion 310 of the piston 304 so that as the piston moves from the non-actuated to the actuated position the projection 326 moves along the threads 328. As the projection 326 moves along the threads 328, the rotatable member 306 rotates relative to the piston 304 and the valve housing 298. The piston 304 is fixed to the housing 298 in order to prevent the rotational movement of the piston relative to the housing. Preferably, the piston 304 is fixed to the housing 298 by side projecting portions 330 engaging groves 332 located in the internal wall 334 of the housing 298. The base 322 of the rotatable member 306 has an opening 336 therethrough for the passage of fluid. In the non-actuated position, the opening 336 is not in fluid communication with the outlet 338 of the housing 298. In the actuated position, the rotatable member 306 is rotated so that the opening 336 communicates with the outlet 338 via a slot 340 in the housing.

The piston 304 and the rotatable member 306 are biased to the non-actuated position by a biasing member. Preferably, the biasing member comprises a spring 342 that is located between the base 322 of the rotatable member 306 and the lower portion 310 of the piston 304. The spring 342 pushes against lower portion 310 of the piston 304 to move the piston 304 back into the non-actuated position, simultaneously rotating the rotatable member 306 back to the non-actuated position.

As shown in FIG. 19, a male luer 344 is inserted through the first valve 300 and into the valve housing 298. The male luer 344 engages the upper portion 308 of the piston 304 and applies downward pressure to move the piston 304 in a downward direction. As the piston 304 moves in a downward direction, the engagement between the threads 328 and the projections 326 of the rotatable member 306 cause the rotatable member to rotate relative to the piston 304 and the housing 298. The rotatable member 306 is rotated until the opening 336 through the base 322 of the rotatable member 306 is aligned with slot 340 in the bottom wall 346 of the housing 298. In this fully actuated position, fluid can be transferred to and from the male luer 344 and through the valve housing 298.

Figure 20:
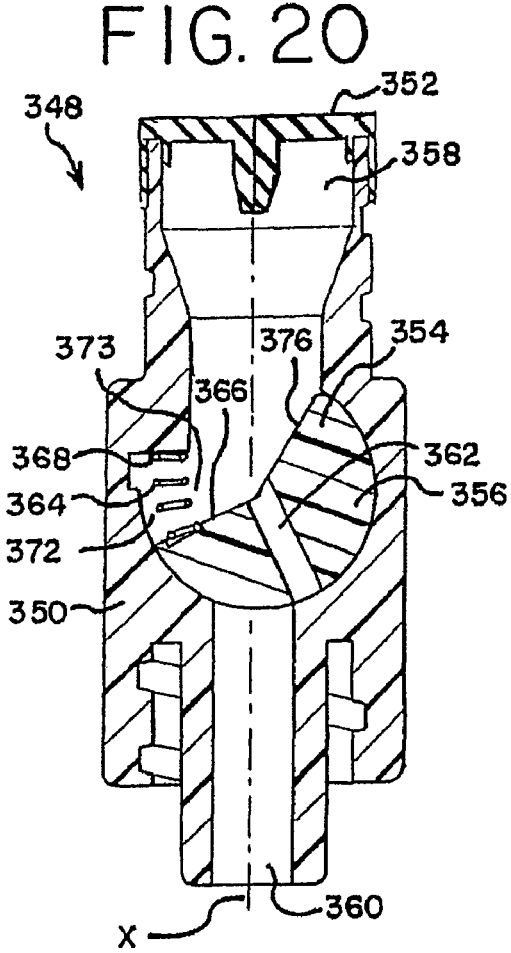
FIG. 20 is a cross-sectional view of another embodiment of a LAD of the present invention.
Figure 21:
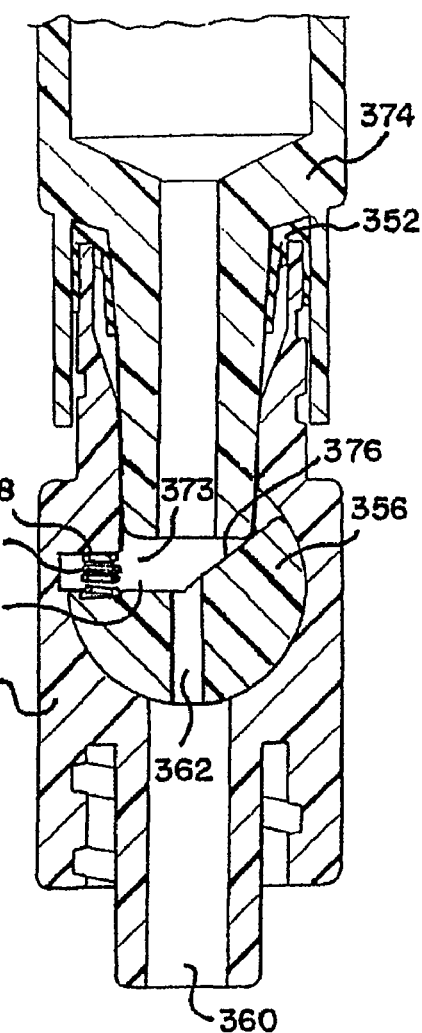
FIG. 21 is a cross-sectional view of the LAD of FIG. 20, shown engaged with a male luer.
Figure 22:
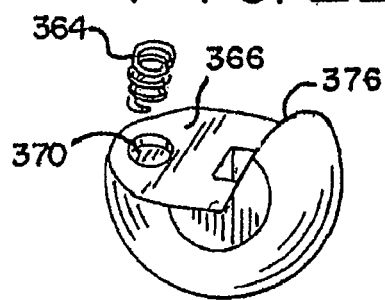
FIG. 22 is a perspective view of one embodiment of one of the valves of the LAD of FIG. 20.

FIGS. 20-22 illustrate another embodiment of the LAD of the present invention, generally designated 348. The LAD includes a housing 350 that is generally similar to the housings of the previous embodiments and includes a first valve 352 and a second valve 354. The first valve 352 is generally similar to the first valves of the previous embodiments and, for example, can be any suitable septum or other type of valve element generally known in the art or described herein.

The second valve 354 comprises a rotatable valve element 356 that has a non-actuated position (FIG. 20) and an actuated position (FIG. 21). The rotatable member 356 rotates between the non-actuated and actuated position along an axis that is generally transverse to a central axis "x" of the valve housing 350. Said central axis being the axis that passes through the inlet 358 and outlet 360 of the valve housing 350. The valve element 356 having fluid flow path 362 extending therethrough. When the fluid flow path 262 is in the non-actuated position, the fluid flow path 362 is orientated so that it is not in communication with the valve housing outlet 360. In the actuated position, the valve element 356 is rotated so that the fluid flow path 362 is aligned with the valve housing outlet 360. The fluid flow path 362 through the valve element 356 preferably has a configuration that minimizes the rotation required to bring the fluid flow path 362 into and out of communication with the valve outlet 360. For example, the fluid flow path 362 of the illustrated embodiment has a rectangular cross-section.

The valve element 356 is biased by a biasing member to the non-actuated position. Preferably, the biasing member is a spring 364 that is positioned between an angled surface 366 of the rotatable member and a surface 368 of the valve housing 350. Preferably, the angle surface 366 of the valve element 356 has an indent 370 for maintaining the spring 364 in position, as illustrated in FIG. 22.

Preferably, the valve element 356 is configured to only allow the rotatable member to rotate about one axis. In the illustrated embodiment, referring to FIG. 22, the valve element 356 has the shape of a sphere having diametrically opposed flat surfaces or, in other words, the shape of a wheel of cheese having an arcuate sidewall. A cavity 373 in the valve housing 350 has a corresponding shape that the valve element occupies and only allows the valve element to rotate about the one axis extending between the flattened ends.

Referring to FIG. 21, in use, a male luer 374 is inserted through the first valve 352 and into the valve housing 350. In the housing 350, the male luer 374 engages a second angled surface 376 and applies downward pressure on the surface 376 which causes the valve element 356 to rotate so that the fluid flow path 362 is in communication with the outlet 360 of the valve housing 350. In this actuated position, the desired amount of fluid can now be transferred out of or into the male luer 374. After the desired amount of fluid is transferred, the male luer 374 is removed from the LAD 348, and the biasing member 364 biases the valve element 356 back to the non-actuated position, wherein the fluid flow path 362 of the valve element 356 is out of fluid communication with the valve outlet 360.

The fluid path 362 of valve element 356 preferably is dimensioned so that only minimal rotation of the valve element is required to actuate and de-actuate the LAD 348. Accordingly, when the male luer is initially withdrawn from the valve housing 350, the valve element 356 rotates and the fluid path 362 is out of fluid communication with the outlet 360. When the fluid path 362 is out of fluid communication with the outlet the space 358 between the first and second valves 352, 354 is also out of fluid communication with the outlet 360. Because of the lack of fluid communication between the space 358 and the outlet 360, further removal of the male luer 374 will not have any net effect on the fluid displacement to or from the outlet 360—thereby reducing reflux.

FIGS. 23 and 24 illustrate another embodiment of a LAD of the present invention generally designated 376. The LAD 376 includes a housing 378 that is generally similar to the housings of the previous embodiments and includes a first valve 380 and a second valve 382. The first valve 380 is generally similar to the first valve 382 of the previous embodiments and, for example, can be any suitable septum or other type of valve element generally known in the art or described herein.

Referring to FIG. 23, the second valve 382 comprises a fluid filled compressible member, such as the illustrated fluid chamber 384. The fluid chamber 384 occupies a portion of the inlet 386 of the valve housing 378, and preferably, engages a circumferential projection 388 of the valve housing 378 to form a fluid seal. The fluid chamber 384 may be filled with any type of fluid and is preferably filled with air. The fluid chamber 384 is in communication with a resilient bladder 390 also located within the housing 378. When the fluid chamber 384 is compressed, fluid from the chamber is displaced into the resilient bladder 390. The bladder 390 preferable has a higher durometer value than the fluid chamber 384, so that when the force compressing the fluid chamber 384 is removed, the bladder 390 constricts displacing the fluid back into the bladder.

Referring to FIG. 24, to actuate the LAD 376 a male luer 392 is inserted through the first valve element 380 and into the inlet 386 of the housing 278. As the male luer 392 is inserted into the inlet 386 of the housing, the male luer 392 compresses the fluid chamber 384 displacing the fluid within the chamber into the bladder 390. Preferably, the volume of the amount of fluid displaced from the fluid chamber 384 is substantially equal to the volume of the portion of the male luer 392 inserted into the housing 378 so that there is a minimal displacement of fluid during insertion and removal of the male luer. After the fluid chamber 384 has been compressed by the male luer 392, fluid can then be transferred to or from the male luer 392. After the desired amount of fluid is transferred, the male luer 392 is withdrawn and the bladder 390 constricts forcing the fluid back into the chamber 384.

FIGS. 25 and 26 illustrate an alternative embodiment of the LAD 376a in which a resilient bladder is not employed, and the chamber 384a is vented to the atmosphere. Preferably, the chamber 384a is attached to the internal wall 394 of the valve housing around vent opening 396. Vent opening 396 is in communication with the atmosphere via outer vent 398 in the outer wall 400 of housing. In another alternative embodiment, the outer vent 398 is covered with a resilient membrane to form a bladder in the valve housing. The resilient membrane expands and contracts as fluid is displaced from the bladder into a chamber.

Turning now to FIGS. 27-43, these figures illustrate different embodiments of LADs that have valves that can be use alone or in conjunction with the above described valves.

FIGS. 27-28 illustrate one embodiment of an LAD of the present invention, generally designated as 402. The LAD includes a housing 404 that is generally similar to the housings of the previous embodiments and includes a valve inlet 406, a valve outlet 408 and a passageway therethrough 410. The LAD 402 includes a valve or septum 412 that seals the valve inlet 406. The valve element 412 is comprised of a plurality layers of material that are bond together, preferably by lamination. In the illustrated embodiment, the valve element 412 contains a first layer 414, a second layer 416 and a third layer 418.

The valve element 412 can be attached to the housing 404 by adhesively bonding periphery of the valve element 412 to the internal wall 420 of the housing or by other suitable well known means. For example, the valve element 412 can be mechanically attached to or captured by the valve housing. Each layer of material includes a resealable aperture or slit 422a, 422b, 422c. Each aperture is preferably generally aligned with the resealable aperture of the adjacent layer. The resealable apertures 422a-c are adapted to receive a male luer 424 therethrough and allow the male luer to enter the flow path 410 of the valve housing.

Each layer of the valve member can be made of a different material. As defined herein "different material" can mean materials comprised of different types of elements, or materials comprised of the same type of element having different characteristics, such as silicone having different durometer values. Preferably, the layers 414, 416, 418 of the valve element are comprised of a polymeric material, such as silicone, or a thermoplastic elastomer, such as thermoplastic polyurethane. Furthermore, each layer 414, 416, 418 can have a different durometer value than the adjacent layer. For example, when the valve element has three layers, the first layer 414 can have a durometer value between about 10 A and about 30 A, the second layer 416 can have a durometer value between about 30 A and about 60 A durometer, and the third layer 418 can have a durometer value between about 60 A and 90 A durometers.

One of the advantages of the multi-layered valve element is that the valve element can be customized for a particular use in that the material's characteristics, such as thickness, durometer valve and type of material, can be chosen to suit the user's needs. For example, it is commonly understood that thicker valve elements are resistant to higher pressures. By employing layers of different durometer values, it is possible to manufacture thinner valve members having a desired pressure resistant quality.

Referring to FIG. 28, in operation, a male luer 424 is inserted through the apertures 422a-c of each of the layers 414, 416, 418 into the fluid path 410 within the valve housing 404. Each layer of the valve member preferably forms a seal with the male luer to prevent leakage. Once inside the fluid path 410, the fluids can be transferred to and from the male luer 424. After the desired amount of fluid is transferred, the male luer is withdrawn and the apertures 422a-c reseal.

FIGS. 29-31 illustrate another embodiment of a LAD of the present invention, generally designated as 426. The LAD includes a housing 428 that is generally similar to the housings of the previous embodiments and includes a valve inlet 430, a valve outlet 432 and a passageway therethrough 434. The LAD 426 also includes a valve element 438 that seals the valve inlet 430. The valve element 438 is comprised a plurality of annular contiguous segments wherein each segment can be comprised of a different material. In the illustrated embodiment, the valve element includes 3 segments 440, 442, 444. The annular contiguous segments 440, 442, 444 are bonded together. This bonding can take place during formation of the valve element. For example, it is known that different types of silicone will naturally bond together during the molding process. Alternatively, the segments can be manufactured and then bonded together.

Preferably, a resealable aperture 446 extends at least through the innermost segment 444. In use, the resealable aperture 446 receives a male luer 448 therethrough, allowing the male luer 448 to access flow path 434 of the housing. Once inside the fluid path 434, fluids can be transferred to and from the male luer 448. After the desired amount of fluid is transferred, the male luer is withdrawn and the resealable aperture 446 reseals.

FIGS. 32 and 33 illustrate another embodiment of a LAD of the present invention, generally designated as 450. The LAD includes a housing 452 that is generally similar to the housings of the previous embodiments and includes a valve inlet 454, a valve outlet 456 and a passageway 458 therethrough. The LAD also includes a valve element 458 that seals the valve inlet 454.

In this embodiment, the valve element 458 is comprised of a plurality of layers, at least two of which are not bonded together, and wherein each layer is individually attached to the valve housing 452. In the illustrated embodiment, the valve element includes a first layer 460, a second layer 462, a third layer 464 and a fourth layer 466. The layers, 460, 462, 464, 466 can be in contact with an adjacent layer or the layers can be spaced apart by some distance. As with the previous embodiment shown in FIGS. 27 and 28, each of the layers 460, 462, 464, 466 can be of a different material and the user can tailor the valve element to the user's need. Moreover, each layer may have laminated sublayers or be made with annular segments, as illustrated in FIGS. 27-31, or any combination of these. Each layer includes a resealable aperture or slit 468a-d. The layers can be aligned so the each slit is aligned perpendicular to the slit of the adjacent layer. Alternatively, each slit can be aligned parallel to and co-planar with the slit of the adjacent layer.

Referring to FIG. 33, in operation, a male luer 470 is inserted through the apertures 468a-d of each of the layers 460, 462, 464, 466 into the fluid path 458 within the valve housing. Once inside the fluid path 458, the fluids can be transferred to and from the male luer. After the desired amount of fluid is transferred, the male luer 470 is withdrawn and the resealable apertures 468 reseal.

FIGS. 34-36 illustrate another embodiment of a LAD of the present invention, generally designated as 472. The LAD includes a housing 474 that is generally similar to the housings of the previous embodiments and includes a valve inlet 476, a valve outlet 478 and a passageway 480 therethrough. The LAD 472 also includes a valve element 482 that seals the valve inlet 476.

In this embodiment, the valve housing 474 includes support members 484 that project into the inlet 476 of the valve housing 474, as shown in FIG. 35. The support members can be integral with the housing or can be attached to the housing. Preferably, the support members have a resilient, spring-like characteristic and are comprised of a plastic material such as ABS. However, the support members could be comprised of a metal or metal alloy. The support members 484 preferably have a thickness of between about 0.002 inch and about 0.010 inch, and preferably protrude into the inlet about a distance of 0.050 inch.

The valve element 482 is preferably comprised of a polymeric material that is overmolded onto the valve housing 474 so that the support members 484 are disposed inside the valve member 482. The valve member 482 includes a resealable aperture 486 for receiving a male luer 488 therethrough. The support members 484 add support to the valve element 482 and allow for the use of thinner valve elements while maintaining same pressure resistant as thicker valve member made out of the same material.

Referring to FIG. 36, in operation, a male luer 488 is inserted through the aperture 486 of the valve element 482 and into the fluid path 476 of the valve housing 474. Once inside the fluid path 480, the fluids can be transferred to and from the male luer 488. After the desired amount of fluid is transferred, the male luer 488 is withdrawn and the support members 484 bias the resealable aperture 486 back to the sealed position.

FIGS. 37-38 illustrate another embodiment of a LAD of the present invention, generally designated as 490. The LAD 490 includes a housing 492 that is generally similar to the housings of the previous embodiments and includes a valve inlet 494, a valve outlet 496 and a passageway 498 therethrough. The LAD 490 also includes a valve element 500 that seals the valve inlet 494.

Referring to FIGS. 37 and 38, in this embodiment, the valve element 500 is comprised of a plurality of discrete particles 502 that are independently movable relative each other within elastomeric pouch or sheath 504, such as a silicone sheath. The particles 502 are preferably plurality of microspheres having a size between about 0.0001 inch (0.0025 mm) and 0.005 inch (0.125 mm). The particles 502 can be polyethylene or glass beads and can be impregnated with an antimicrobial agent that is permitted to leach out of the elastomeric sheath 504. The valve element 500 includes a resealable aperture 506 therethrough, which is defined by the sheath and adapted to receive a male luer 508 therethrough.

Preferably, the valve element 500 has general hourglass shape and is bonded to the valve housing 492 around the periphery of the top 510 and the periphery of the bottom 512 of the valve element by adhesive or other suitable bonding. The arcuate portions 514 or "waist" of the hourglass shaped valve element 500 define a space 515 between the valve element 500 and the valve housing 492 that may be vented through the vent openings 516 located in the valve housing.

Referring to FIGS. 38 and 39, in use, a male luer 508 is inserted into the resealable aperture 506 of the valve element 500. As the male luer 508 is inserted, the particles 502 are pushed out of the way, displacing the particles and a portion of the sheath into the space 515. As a portion of the valve element is displaced into the space 515, the fluid within the space is displaced to the atmosphere through vents 516. Preferably, the volume of the displaced portion of the valve element 500 is substantially equal to the volume of the portion of the male luer 508 that is inserted into the valve housing 492, thereby resulting in a minimal displacement of fluid during insertion and withdrawal of the male luer. Once the male luer 508 is inside the fluid path 498, fluids can be transferred to and from the male luer 508. After the desired amount of fluid is transferred, the male luer 508 is withdrawn and the resiliency of the sheath 504 causes the valve element 500 to reform into its hourglass shape.

FIGS. 40 and 41 illustrate another embodiment of a LAD of the present invention, generally designated as 520. The LAD 520 includes a housing 522 that is generally similar to the housings of the previous embodiments and includes a valve inlet 524, a valve outlet 526 and a flow path 528 therethrough. The LAD 520 also includes a valve element 530 that seals the valve inlet 524.

In this embodiment, the valve element 530 an aperture 532 (shown in phantom) through the valve element 530 that follows a contorted path, which is preferably helical corkscrewed-shaped. In one method of manufacturing the valve element 530, the valve element is twisted to a distorted configuration and then a slit is sliced through the valve element to create the resealable aperture 532. The valve element 530 is then released and allowed to twist back into its original configuration thereby contorting the path of the aperture 532. The contoured path of the aperture 532 creates multiple seals having different orientations throughout the path of the aperture. These multiple seals enhance the valve elements resistance to back pressure.

As illustrated, the periphery of the top 534 of the valve element 530 is attached to the valve housing inlet 524, preferably by adhesive bonding or any other type of bonding known in the art, such as overmolding. The bottom 536 of the valve element 530 is not attached to the valve housing 522 so that the bottom 536 of the valve element 530 is able to be rotated relative to top 534 of the valve element 530 and the valve housing 522. Referring to FIG. 41, a male luer 538 is inserted into aperture 532. As the male luer 538 is inserted, the bottom 536 of the valve element 530 rotates relative to the top 534 of the valve element 530, thereby at least partially straightening the contorted opening the aperture 532. When the aperture 532 is straightened and open, the male luer 538 is allowed to communicate with the flow path 528 for the transfer of fluids to and from the male luer. After the male luer 538 is removed, the valve member 530 returns to its original configuration with a contorted slit therethrough.

FIGS. 42 and 43 illustrate yet another embodiment of a LAD of the present invention, generally designated 540. The LAD 540 includes a housing 542 that is generally similar to the housings of the previous embodiments and includes a valve inlet 544, a valve outlet 546 and a flow path 548 therethrough. This LAD is described in more detail in U.S. patent application Ser. No. 11/550,570, entitle "Luer Activated Device With Compressible Valve Element" filed simultaneously herewith, and hereby incorporated by reference.

The inlet 544 fixedly receives a deformable valve or septum 550 having a slit or aperture 552 therethrough. The septum 550 acts as a microbial barrier between the internal fluid flow path 548 of the LAD 540 and the atmosphere. The septum 550 preferably includes a substantially flat outside surface that can be easily wiped with antiseptic, which aids in preventing contamination during use. The septum 550 may be fixedly attached to the inlet 544 by any of a number of means. Suitable means include, but are not limited to, adhesion, mechanical bonding, and interference overmolding. Preferably, the septum 550 is slightly larger than the inlet 544, such that it is radially compressed to some extent in the closed condition of FIG. 42. Imparting such compression to the septum 550 promotes an improved seal of the resealable septum slit 40, thereby preventing fluid leakage through the inlet 544.

The septum slit 552 is adapted to accept the male luer 554 and allow the male luer 554 to access the interior of the LAD 540. The slit 552 may be integrally formed, e.g., molded, with the septum 552 or may be formed after the septum 550 is seated within the inlet 544.

In a closed or uncompressed condition (FIG. 42) the septum 550 assumes a substantially cylindrical shape to close the slit 552 and prevent fluid flow through the inlet 544. In an open or compressed condition (FIG. 43), the septum 550 is forced into a deformed, tubular shape by the male luer 554 received by the slit 552. The radius of the inlet 544 is greater than the radius of the male luer 545, and the deformed septum 550 of FIG. 43 occupies and seals the space therebetween to prevent fluid leakage from the inlet 544.

The septum 550 is substantially comprised of a deformable, compressible material. When used herein, the term "compressible" refers to a material that is capable of decreasing in volume by more than a nominal amount upon insertion of a male luer 554 into the inlet 544 (FIG. 43). For example, a silicone or elastomeric split septum according to known structure and operation is deformable, because it will change shape to accommodate a male luer, but it is not compressible because it is not capable of a substantial reduction in volume. Those of ordinary skill in the art will appreciate that, when using known elastomeric split septums, the open internal volume of the valve (i.e., the portion of the valve interior that is available for fluid flow) will substantially decrease upon insertion of a male luer, because the valve interior must receive the combined volumes of the male luer and the deformed septum, instead of just the volume of the septum. This change in open internal volume will impart a positive displacement of fluid during the insertion and removal of the male luer, which affects flow dynamics and may be undesirable in certain applications.

Through the use of a compressible septum 550, the change in available flow path volume from V (FIG. 42) to V' (FIG. 43) may be minimized to avoid the effects of positive fluid displacement. The pre-insertion open internal volume V is substantially equal to the volume of the housing interior less the volume of the closed septum 550 (FIG. 42), while the post-insertion open internal volume V is equal to the volume of the housing interior less the combined volume of the portion of the male luer 554 received within the housing 542 and the volume of the deformed septum 540. From the foregoing relationship, it will be seen that the volume of the closed septum 540 (FIG. 42) is preferably about equal to the sum of the volumes of the deformed septum 550 and the portion of the male luer 554 received within the LAD housing 542 (FIG. 43) to eliminate any change in open internal volume before and after insertion of the male luer 554. This relationship may be manipulated by changing any of a number of factors, including the size of the luer portion received by the inlet 544, the difference in radii between the inlet 544 and the luer wall 545, and the thickness T of the septum 550.

Another benefit of using a compressible material instead of a solely deformable material is that the septum 550 is subjected to less shear stress upon insertion of the male luer 554 and tends to be more durable. In particular, it will be appreciated by those of ordinary skill in the art that a typical rubber or silicone split septum is significantly stretched and deformed upon insertion of a male luer, which puts the material primarily in a state of shear stress. In contrast, septa according to the present invention are primarily radially compressed by the male luer 554, with a smaller degree of deformation and shear stress. Accordingly, the majority of the stress is transmitted to the bonding material between the septum 550 and the inlet 544, which is significantly stronger in compression than a rubber or silicone septum is in shear, so the septum 550 is more durable than known rubber or silicone septa.

Preferably, the septum 550 is substantially comprised of a compressible polymeric foam, such as a silicone or urethane foam. The foam may be provided with a closed- or open-cell structure, depending on the intended use of the LAD 540. A closed-cell structure is typically more rigid and less compressible than an open-cell structure, so such a configuration may be preferred for application requiring less deformation of the septum 540, such as when the valve 10 is used in combination with a male luer 554 having a relatively small radius.

Open-cell foams may be used in applications requiring more deformation, such as when the valve 540 is used in combination with a male luer 554 having a relatively large radius. Open-cell foams also allow for other variations that are not possible or not as practicable with closed-cell foams. For example, an open-cell foam may be impregnated with a liquid or gelatinous material having anti-microbial, anti-clotting, lubricating, or other properties. When the male luer 554 is inserted into the slit 552, the septum 550 is compressed, thereby applying the material to the male luer 554, the flow path 548, or the fluid being transferred through the valve 540.

While open-cell foams are potentially more versatile in certain respects than closed-cell foams, there is the risk that the open cells may allow fluid leakage through the inlet 544, especially in the uncompressed condition of FIG. 42. To prevent such leakage, an open-cell foam may be treated with a substantially closed outer layer or skin (not illustrated), which may be applied by any of a number of methods, including dipping. Preferably, such a skin is sufficiently porous to allow elution of a material impregnated within the foam, without allowing fluid leakage through the inlet 544. Suitable skin materials include ePTFE and silicone. While such surface treatment is more preferred for use with open-cell foams, a skin or outer layer may also be applied to a closed-cell foam (not illustrated). The skin may have different characteristics than the underlying septum 540, to make it easier to insert or remove the male luer 554, for example.

In an alternative embodiment of LAD suitable for use with an open-cell foam, the inlet 544 includes at least one vent through the inlet 544 that allows for communication between the septum 550 and the atmosphere. In the uncompressed condition air is maintained within the open cells of the foam. When the male luer 554 is at least partially inserted into the slit 552 of the septum 550, the open cells are compressed and the air maintained therein is vented to the atmosphere through the vents. If the septum 550 is provided with a skin or outer layer, then the portion adjacent to the vents is preferably uncoated to promote aspiration of the foam.

While the present invention has been described in terms of certain preferred and alternative embodiments for purposes of illustration, it is not limited to the precise embodiments shown or to the particular features, shapes or sizes illustrated. A variety of changes may be made without departing from the present invention as defined by the appended claims.

The invention claimed is:

1. A medical valve for the transfer of fluid, comprising:
   a housing having an inlet, an outlet and a flow path defined therebetween; and
   a valve configured to seal the inlet of said housing, said valve comprising a plurality of discrete particles, wherein the discrete particles include microspheres that are free to move in relation to one another within a chamber, and wherein said valve includes a resealable aperture configured to receive insertion of a male luer through the valve inlet.

2. The medical valve of claim 1 in which the microspheres are impregnated with an antimicrobial agent.

3. The medical valve of claim 1 in which the particles have a size of about 0.0001 inches to about 0.0005 inches.

4. The medical valve of claim 1 in which the particles are comprised of glass beads, polymer beads or mixture of glass beads and polymer beads.

5. The medical valve of claim 1 in which the valve comprises an elastic outer wall defining an internal chamber containing the particles.

6. A medical valve for the transfer of fluid comprising:
   a housing having an inlet, an outlet and a flow path defined therebetween; and
   a valve including a normally closed position that seals the inlet of the housing, the valve having a valve inlet and comprising a plurality of discrete particles that move within a chamber to accommodate insertion of a flow member through a resealable aperture of the valve inlet, wherein:
   (a) the discrete particles include microspheres, and (b) the valve is in an open position when the flow member is inserted into the valve inlet via the resealable aperture thereby displacing the plurality of discrete particles, unsealing the valve inlet and allowing the transfer of fluid through the flow member to the flow path.

7. The medical valve of claim 6 in which the microspheres are impregnated with an antimicrobial agent.

8. The medical valve of claim 6 in which the particles have a size of about 0.0001 inches to about 0.0005 inches.

9. The medical valve of claim 6 in which the particles are comprised of glass beads, polymer beads or mixture of glass beads and polymer beads.

10. The medical valve of claim 6 wherein the chamber includes an elastomeric wall containing the particles.

11. The medical valve of claim 10 wherein the elastomeric wall has a resiliency urging the contained particles to close the valve absent any applied force.

12. The medical valve of claim 11 wherein when the insertion force is applied to the flow member, the resiliency is overcome and the contained particles are displaced, placing the valve in the open position.

13. The medical valve of claim 11 wherein, upon withdrawal of the male luer from the valve inlet, the resiliency causes the elastomeric wall containing the particles to close the valve, thereby preventing the transfer of fluid through the flow path.

14. The medical valve of claim 11 in which the elastomeric wall is comprised of a silicon sheath.

* * * * *